US010863970B2

(12) United States Patent
Oberg et al.

(10) Patent No.: US 10,863,970 B2
(45) Date of Patent: Dec. 15, 2020

(54) NEEDLE GUIDE INCLUDING ENHANCED VISIBILITY ENTRANCE

(71) Applicant: C. R. Bard, Inc., Franklin Lakes, NJ (US)

(72) Inventors: Kevin M. Oberg, Clinton, MS (US); Jason R. Stats, Layton, UT (US); Amir Orome, Sandy, UT (US); Jon B. Newman, Centerville, UT (US); Jonathan C. Gorzitze, Kaysville, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 675 days.

(21) Appl. No.: 14/581,019

(22) Filed: Dec. 23, 2014

(65) Prior Publication Data

US 2015/0112200 A1 Apr. 23, 2015

Related U.S. Application Data

(60) Continuation of application No. 29/493,150, filed on Jun. 5, 2014, now Pat. No. Des. 752,743, which is a
(Continued)

(51) Int. Cl.
*A61B 8/14* (2006.01)
*A61B 8/00* (2006.01)
(Continued)

(52) U.S. Cl.
CPC ............ *A61B 8/467* (2013.01); *A61B 8/0841* (2013.01); *A61B 8/4444* (2013.01);
(Continued)

(58) Field of Classification Search
None
See application file for complete search history.

(56) References Cited

U.S. PATENT DOCUMENTS

| | | |
|---|---|---|
| 2,470,488 A | 5/1949 | Honerkamp et al. |
| 4,058,114 A | 11/1977 | Soldner |
| | (Continued) | |

FOREIGN PATENT DOCUMENTS

| | | |
|---|---|---|
| CN | 3655315 | 6/2007 |
| DE | 2942405 A1 | 4/1981 |
| | (Continued) | |

OTHER PUBLICATIONS

U.S. Appl. No. 13/886,196, filed May 2, 2013 Examiner's Answer dated Nov. 3, 2015.
(Continued)

*Primary Examiner* — Mark D Remaly
(74) *Attorney, Agent, or Firm* — Rutan & Tucker LLP

(57) ABSTRACT

Needle guide systems for a sonography device are disclosed. The needle guide systems include both fixed and adjustable needle guides. In one embodiment, the needle guide includes a needle guide body that is rotatably mounted to a probe of a sonography device. A plurality of needle channels is disposed on a surface of the needle guide body. Each needle channel can be selectively rotated into position to guide a needle into a body of a patient at a predetermined needle insertion angle. If another needle insertion angle is desired, the needle guide is rotated to place a new needle channel defining the desired needle insertion angle into position. In another embodiment, a needle guide is disclosed and includes an extended guide feature, such as a guide cone, to assist in inserting a needle into the needle channel.

22 Claims, 25 Drawing Sheets

Related U.S. Application Data continuation of application No. 13/886,196, filed on May 2, 2013, now Pat. No. 10,231,697, which is a division of application No. 12/642,456, filed on Dec. 18, 2009, now Pat. No. 8,574,160.

(60) Provisional application No. 61/138,606, filed on Dec. 18, 2008, provisional application No. 61/920,242, filed on Dec. 23, 2013.

(51) Int. Cl.
  A61B 8/08 (2006.01)
  A61B 90/11 (2016.01)
  A61B 90/00 (2016.01)

(52) U.S. Cl.
  CPC ............ *A61B 8/4455* (2013.01); *A61B 8/461* (2013.01); *A61B 90/11* (2016.02); *A61B 8/4411* (2013.01); *A61B 8/4427* (2013.01); *A61B 2090/067* (2016.02); *A61B 2090/378* (2016.02)

(56) References Cited

U.S. PATENT DOCUMENTS

| | | | |
|---|---|---|---|
| 4,108,165 | A | 8/1978 | Kopp et al. |
| 4,341,303 | A | 7/1982 | Britt |
| 4,346,717 | A | 8/1982 | Haerten |
| 4,363,326 | A | 12/1982 | Kopel |
| 4,402,324 | A | 9/1983 | Lindgren et al. |
| 4,408,611 | A | 10/1983 | Enjoji |
| 4,469,106 | A | 9/1984 | Harui |
| 4,497,325 | A | 2/1985 | Wedel |
| 4,548,210 | A | 10/1985 | Enjoji et al. |
| 4,576,175 | A | 3/1986 | Epstein |
| 4,582,326 | A | 4/1986 | Alsip |
| 4,608,989 | A | 9/1986 | Drue |
| 4,635,644 | A | 1/1987 | Yagata |
| 4,662,870 | A | 5/1987 | Augustine et al. |
| 4,681,103 | A | 7/1987 | Boner et al. |
| 4,723,544 | A | 2/1988 | Moore et al. |
| 4,742,829 | A | 5/1988 | Law et al. |
| 4,838,506 | A | 6/1989 | Cooper |
| 4,877,033 | A | 10/1989 | Seitz, Jr. |
| 4,883,059 | A | 11/1989 | Stedman et al. |
| 4,898,178 | A | 2/1990 | Wedel |
| 4,899,756 | A | 2/1990 | Sonek |
| 4,911,173 | A | 3/1990 | Terwilliger |
| 5,052,396 | A | 10/1991 | Wedel et al. |
| 5,076,279 | A | 12/1991 | Arenson et al. |
| 5,100,387 | A | 3/1992 | Ng |
| 5,138,748 | A | 8/1992 | Welles |
| 5,235,987 | A | 8/1993 | Wolfe |
| 5,265,614 | A | 11/1993 | Hayakawa et al. |
| 5,280,427 | A | 1/1994 | Magnusson et al. |
| 5,427,108 | A | 6/1995 | Bollinger |
| D362,064 | S | 9/1995 | Smick |
| 5,494,039 | A | 2/1996 | Onik et al. |
| 5,623,931 | A | 4/1997 | Wung et al. |
| 5,758,650 | A | 6/1998 | Miller et al. |
| D399,971 | S | 10/1998 | Scherer |
| 5,911,707 | A | 6/1999 | Wolvek et al. |
| D412,032 | S | 7/1999 | Mikula-Curtis et al. |
| 5,924,992 | A | 7/1999 | Park et al. |
| 5,941,889 | A | 8/1999 | Cermak |
| 6,050,954 | A | 4/2000 | Mittermeier |
| D424,693 | S | 5/2000 | Pruter |
| 6,083,169 | A | 7/2000 | Hansen |
| 6,095,981 | A | 8/2000 | McGahan |
| D434,850 | S | 12/2000 | Balestracci |
| 6,203,499 | B1 | 3/2001 | Imling et al. |
| 6,283,942 | B1 | 9/2001 | Staehlin et al. |
| 6,296,614 | B1 | 10/2001 | Pruter |
| 6,361,499 | B1 | 3/2002 | Bates et al. |
| 6,368,280 | B1 | 4/2002 | Cermak et al. |
| 6,379,307 | B1 | 4/2002 | Filly et al. |
| 6,425,871 | B1 | 7/2002 | Jaggi |
| 6,475,152 | B1 | 11/2002 | Kelly, Jr. et al. |
| 6,485,426 | B2 | 11/2002 | Sandhu |
| 6,500,119 | B1 * | 12/2002 | West ............... A61B 5/0053 600/437 |
| 6,612,990 | B1 | 9/2003 | Pruter |
| 6,695,786 | B2 | 2/2004 | Wang et al. |
| 6,743,177 | B2 | 6/2004 | Ito et al. |
| 6,758,817 | B1 | 7/2004 | Pruter et al. |
| 6,814,704 | B2 | 11/2004 | Weilandt |
| 6,840,954 | B2 | 1/2005 | Dietz et al. |
| 6,877,352 | B1 | 4/2005 | Schlereth |
| 6,884,219 | B1 | 4/2005 | Pruter |
| 6,908,433 | B1 | 6/2005 | Pruter |
| 7,022,082 | B2 | 4/2006 | Sonek |
| 7,087,024 | B1 | 8/2006 | Pruter |
| 7,322,990 | B1 | 1/2008 | Mark et al. |
| 7,351,205 | B2 | 4/2008 | Szczech et al. |
| 7,452,331 | B1 * | 11/2008 | Pruter ............... A61B 8/0833 600/433 |
| 7,588,541 | B2 | 9/2009 | Floyd et al. |
| 7,635,336 | B1 | 12/2009 | Pruter |
| 7,670,294 | B2 | 3/2010 | Kisen et al. |
| 7,691,066 | B2 | 4/2010 | Kosaku |
| D625,802 | S | 10/2010 | Choi et al. |
| D625,805 | S | 10/2010 | Hereford |
| 7,837,627 | B1 | 11/2010 | Pruter |
| D629,898 | S | 12/2010 | Bigelow |
| D630,731 | S | 1/2011 | Schmutzer et al. |
| 7,909,815 | B2 | 3/2011 | Whitmore, III et al. |
| 7,976,469 | B2 | 7/2011 | Bonde et al. |
| D649,245 | S | 11/2011 | Klebs et al. |
| 8,073,529 | B2 | 12/2011 | Cermak et al. |
| 8,075,495 | B2 | 12/2011 | Andreyko et al. |
| 8,118,743 | B2 | 2/2012 | Park et al. |
| D655,813 | S | 3/2012 | Row et al. |
| 8,137,281 | B2 | 3/2012 | Huang et al. |
| D659,825 | S | 5/2012 | Dillard, III |
| D672,460 | S | 12/2012 | Baid |
| 8,430,889 | B2 | 4/2013 | Zeng et al. |
| D683,019 | S | 5/2013 | Shahidi Bonjar |
| 8,496,593 | B2 | 7/2013 | Park et al. |
| 8,523,824 | B2 | 9/2013 | Teirstein et al. |
| 8,641,620 | B2 | 2/2014 | Lasser et al. |
| 8,647,280 | B2 | 2/2014 | Ooishi et al. |
| 8,696,583 | B2 | 4/2014 | Ohgishi et al. |
| 8,696,585 | B2 | 4/2014 | Addison et al. |
| 8,708,916 | B2 | 4/2014 | Okuno |
| 8,740,800 | B2 | 6/2014 | Wakabayashi et al. |
| 8,747,324 | B1 | 6/2014 | Pruter et al. |
| D710,995 | S | 8/2014 | Shirley et al. |
| 8,795,183 | B2 | 8/2014 | Siebrecht et al. |
| 8,808,186 | B2 | 8/2014 | Fruland et al. |
| D727,495 | S | 4/2015 | Bown et al. |
| 9,788,812 | B2 | 10/2017 | Orome et al. |
| 9,974,516 | B2 | 5/2018 | Orome et al. |
| 10,231,697 | B2 | 3/2019 | Gorzitze |
| 2002/0123689 | A1 | 9/2002 | Furia |
| 2002/0133079 | A1 | 9/2002 | Sandhu |
| 2003/0144627 | A1 | 7/2003 | Woehr et al. |
| 2003/0195425 | A1 | 10/2003 | Ito |
| 2004/0133111 | A1 | 7/2004 | Szczech et al. |
| 2005/0059891 | A1 | 3/2005 | Kosaku |
| 2005/0113816 | A1 | 5/2005 | Whitmore et al. |
| 2005/0143753 | A1 | 6/2005 | Whitmore et al. |
| 2005/0267373 | A1 | 12/2005 | Lee |
| 2006/0129046 | A1 | 6/2006 | Stevens et al. |
| 2006/0150876 | A1 | 7/2006 | Green et al. |
| 2006/0241477 | A1 | 10/2006 | Sasady et al. |
| 2007/0016781 | A1 | 1/2007 | Asokan et al. |
| 2007/0038113 | A1 | 2/2007 | Oonuki et al. |
| 2007/0073155 | A1 | 3/2007 | Park et al. |
| 2007/0078346 | A1 | 4/2007 | Park et al. |
| 2007/0112272 | A1 | 5/2007 | Park et al. |
| 2007/0167817 | A1 | 7/2007 | Huang et al. |
| 2007/0276241 | A1 | 11/2007 | Park et al. |
| 2007/0276253 | A1 | 11/2007 | Park et al. |
| 2007/0282205 | A1 | 12/2007 | Furia |

(56) References Cited

U.S. PATENT DOCUMENTS

| | | |
|---|---|---|
| 2008/0033454 A1 | 2/2008 | Lukoschek et al. |
| 2008/0300491 A1 | 12/2008 | Bowie et al. |
| 2009/0143684 A1 | 6/2009 | Cermak et al. |
| 2009/0171219 A1 | 7/2009 | Uchibori |
| 2009/0247876 A1 | 10/2009 | Cannon, Jr. et al. |
| 2009/0266957 A1 | 10/2009 | Cermak |
| 2009/0270722 A1 | 10/2009 | Floyd et al. |
| 2009/0275833 A1 | 11/2009 | Ikeda et al. |
| 2010/0010475 A1 | 1/2010 | Teirstein et al. |
| 2010/0041990 A1 | 2/2010 | Schlitt et al. |
| 2010/0081920 A1 | 4/2010 | Whitmore, III et al. |
| 2010/0106056 A1 | 4/2010 | Norris |
| 2010/0160787 A1 | 6/2010 | Gorzitze |
| 2010/0228131 A1 | 9/2010 | Oonuki et al. |
| 2010/0247513 A1 | 9/2010 | Agee et al. |
| 2010/0312121 A1 | 12/2010 | Guan |
| 2011/0028847 A1 | 2/2011 | Whitmore, III et al. |
| 2012/0165679 A1 | 6/2012 | Orome et al. |
| 2012/0330159 A1 | 12/2012 | Orome et al. |
| 2013/0150714 A1 | 6/2013 | Howlett et al. |
| 2013/0245452 A1 | 9/2013 | Gorzitze |
| 2015/0025315 A1* | 1/2015 | Nishina ............... A61B 1/018 600/104 |
| 2019/0209120 A1 | 7/2019 | Gorzitze |

FOREIGN PATENT DOCUMENTS

| | | |
|---|---|---|
| EP | 1709919 A1 | 10/2006 |
| JP | 01097440 A | 4/1989 |
| JP | 03173542 A | 7/1991 |
| JP | 11128237 A | 5/1999 |
| JP | 21161683 | 6/2001 |
| JP | 21340334 | 12/2001 |
| JP | 23299654 | 10/2003 |
| JP | 23334191 | 11/2003 |
| JP | 2005-034273 A | 2/2005 |
| JP | D1268564 | 4/2006 |
| JP | 2009-153831 A | 7/2009 |
| JP | 2010-115246 A | 5/2010 |
| WO | 1996010958 A2 | 4/1996 |
| WO | 2000019906 | 4/2000 |
| WO | 2000040155 A1 | 7/2000 |
| WO | 2003094701 A2 | 11/2003 |
| WO | 2004021898 A1 | 3/2004 |
| WO | 2006060657 A2 | 6/2006 |
| WO | 2007027511 A2 | 3/2007 |
| WO | 2007040172 A1 | 4/2007 |
| WO | 2007110076 A1 | 10/2007 |
| WO | 2008024515 A2 | 2/2008 |
| WO | 2009073653 A1 | 6/2009 |
| WO | 2009090230 A1 | 7/2009 |
| WO | 2010080637 A1 | 7/2010 |
| WO | 2010084322 A1 | 7/2010 |
| WO | 2012088458 | 6/2012 |
| WO | 2012178109 | 12/2012 |
| WO | 2013054168 A2 | 4/2013 |
| WO | 2015100332 A1 | 7/2015 |

OTHER PUBLICATIONS

CN 201180067467.2 filed Aug. 13, 2013 second Office Action dated Apr. 30, 2015.

CN 201280030885.9 filed Dec. 23, 2013 First Office Action dated Mar. 3, 2015.

EP 11 850 516.3 filed Jul. 19, 2013 Extended European Search Report dated Mar. 4, 2015.

EP 12 803 493.1 filed Jan. 15, 2014 Extended European Search Report dated Mar. 5, 2015.

PCT/US2014/072168 filed Dec. 23, 2014 International Search Report and Written Opinion dated Apr. 16, 2015.

U.S. Appl. No. 13/335,587, filed Dec. 22, 2011 Final Office Action dated Jul. 8, 2015.

U.S. Appl. No. 13/335,587, filed Dec. 22, 2011 Non-Final Office Action dated Feb. 2, 2015.

U.S. Appl. No. 13/531,406, filed Jun. 22, 2012 Non-Final Office Action dated Jan. 9, 2015.

U.S. Appl. No. 13/886,196, filed May 2, 2013 Final Office Action dated Dec. 22, 2014.

CN 201180067467.2 filed Aug. 13, 2013 First Office Action dated Sep. 4, 2014.

U.S. Appl. No. 13/886,196, filed May 2, 2013 Advisory Action dated Jun. 13, 2014.

U.S. Appl. No. 13/886,196, filed May 2, 2013 Non-Final Office Action dated Jul. 25, 2014.

EP 14875859.2 filed Jun. 9, 2016 Extended European Search Report dated Jul. 31, 2017.

U.S. Appl. No. 13/335,587, filed Dec. 22, 2011 Decision on Appeal dated Oct. 25, 2017.

CN 201180067467.2 filed Aug. 13, 2013 Third Office Action dated Oct. 28, 2015.

CN 201280030885.9 filed Dec. 23, 2013 Second Office Action dated Nov. 4, 2015.

CN 201280030885.9 filed Dec. 23, 2013 Third Office Action dated May 5, 2016.

JP 2013-546435 filed Jun. 6, 2013 Office Action dated Aug. 29, 2016.

JP 2014-517229 filed Dec. 20, 2013 First Office Action dated May 24, 2016.

JP 2014-517229 filed Dec. 20, 2013 Notice of Allowance dated Oct. 3, 2016.

PCT/US2009/068828 filed Dec. 18, 2009 International Preliminary Report on Patentability dated Jun. 21, 2011.

PCT/US2009/068828 filed Dec. 18, 2009 Search Report dated Mar. 3, 2010.

PCT/US2009/068828 filed Dec. 18, 2009 Written Opinion dated Mar. 3, 2010.

PCT/US2011/066940 filed Dec. 22, 2011 International Preliminary Report on Patentability dated Jul. 4, 2013.

PCT/US2011/066940 filed Dec. 22, 2011 International Search Report and Written Opinion dated Apr. 20, 2012.

PCT/US2012/043877 filed Jun. 22, 2012 International Search Report and Written Opinion dated Sep. 24, 2012.

U.S. Appl. No. 12/642,456, filed Dec. 18, 2009 Final Office Action dated Nov. 23, 2012.

U.S. Appl. No. 12/642,456, filed Dec. 18, 2009 Non-Final Office Action dated Jul. 2, 2012.

U.S. Appl. No. 12/642,456, filed Dec. 18, 2009 Notice of Allowance dated Jul. 12, 2013.

U.S. Appl. No. 13/335,587, filed Dec. 22, 2011 Examiner's Answer dated May 16, 2016.

U.S. Appl. No. 13/335,587, filed Dec. 22, 2011 Final Office Action dated Jul. 28, 2014.

U.S. Appl. No. 13/335,587, filed Dec. 22, 2011 Non-Final Office Action dated Mar. 12, 2014.

U.S. Appl. No. 13/531,406, filed Jun. 22, 2012 Advisory Action dated May 3, 2017.

U.S. Appl. No. 13/531,406, filed Jun. 22, 2012 Final Office Action dated Feb. 25, 2016.

U.S. Appl. No. 13/531,406, filed Jun. 22, 2012 Final Office Action dated Feb. 27, 2017.

U.S. Appl. No. 13/531,406, filed Jun. 22, 2012 Non-Final Office Action dated Aug. 10, 2016.

U.S. Appl. No. 13/531,406, filed Jun. 22, 2012 Non-Final Office Action dated Aug. 18, 2015.

U.S. Appl. No. 13/531,406, filed Jun. 22, 2012 Notice of Allowance dated Jun. 20, 2017.

U.S. Appl. No. 13/886,196, filed May 2, 2013 Final Office Action dated Apr. 10, 2014.

U.S. Appl. No. 13/886,196, filed May 2, 2013 Non-Final Office Action dated Dec. 19, 2013.

U.S. Appl. No. 29/493,150, filed Jun. 5, 2014 Notice of Allowance dated Oct. 29, 2015.

CN 201480070757.6 filed Jun. 23, 2016 Office Action dated Aug. 31, 2018.

(56) References Cited

OTHER PUBLICATIONS

KR 10-2014-7001756 filed Jan. 22, 2014 Office Action dated May 18, 2018.
U.S. Appl. No. 13/335,587, filed Dec. 22, 2011 Notice of Allowance dated Jan. 17, 2018.
U.S. Appl. No. 13/886,196, filed May 2, 2013 Decision on Appeal dated Nov. 20, 2017.
CN 201480070757.6 filed Jun. 23, 2016 Office Action dated May 17, 2019.

* cited by examiner

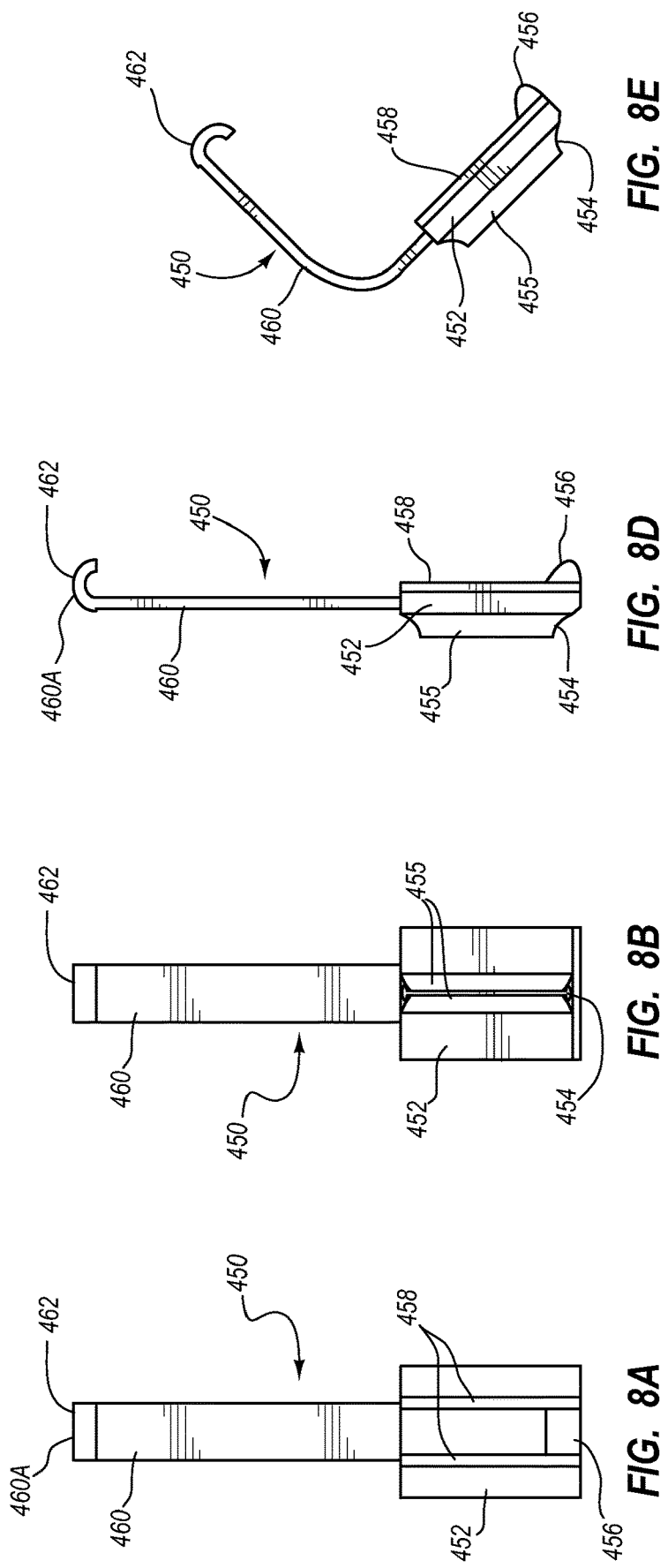

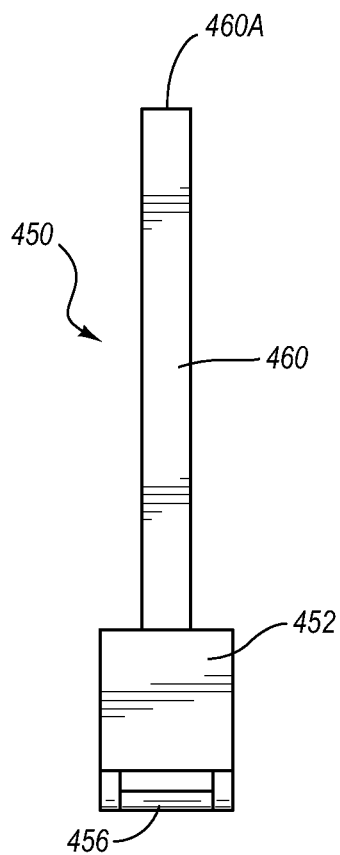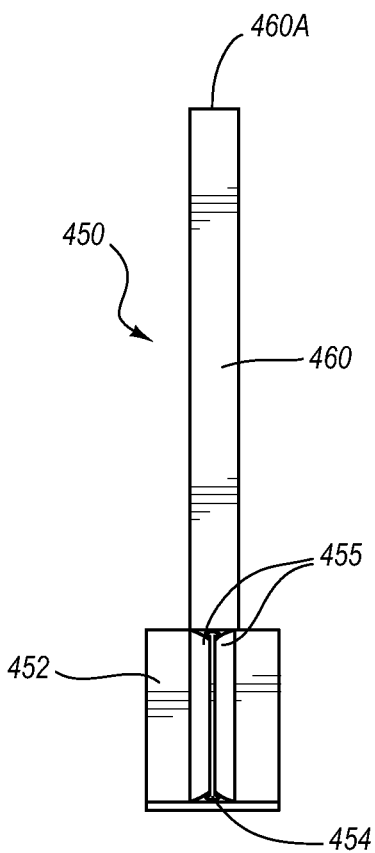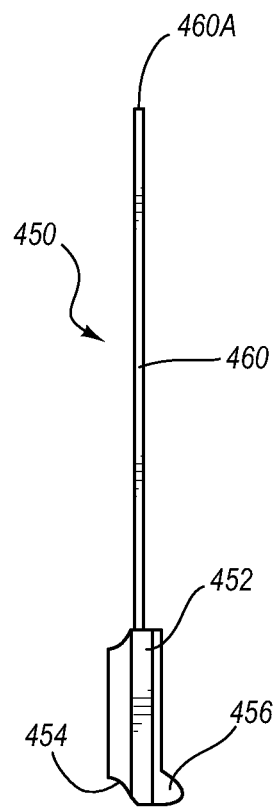
FIG. 9A    FIG. 9B    FIG. 9C
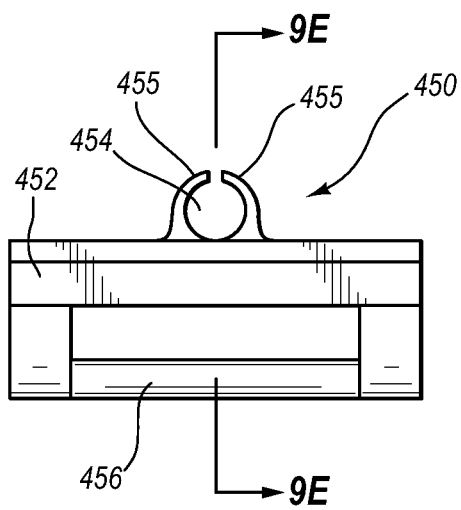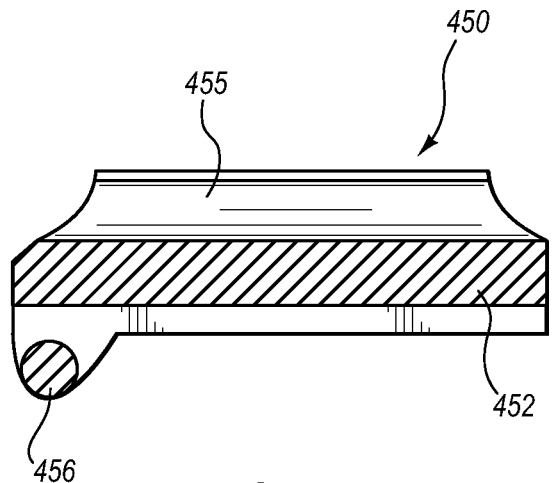
FIG. 9D    FIG. 9E

NEEDLE GUIDE INCLUDING ENHANCED VISIBILITY ENTRANCE

CROSS-REFERENCE TO RELATED APPLICATIONS

This application is a continuation-in-part of U.S. Design patent application Ser. No. 29/493,150, filed Jun. 5, 2014, now U.S. Pat. No. D752,743, which is a continuation of U.S. patent application Ser. No. 13/886,196, filed May 2, 2013, now U.S. Pat. No. 10,231,697, which is a division of U.S. patent application Ser. No. 12/642,456, filed Dec. 18, 2009, now U.S. Pat. No. 8,574,160, which claims the benefit of U.S. Provisional Patent Application No. 61/138,606, filed Dec. 18, 2008. This application also claims the benefit of U.S. Provisional Patent Application No. 61/920,242, filed Dec. 23, 2013. Each of the aforementioned applications is incorporated herein by reference in its entirety.

BRIEF SUMMARY

Briefly summarized, embodiments of the present invention are directed to needle guide systems for a sonography device. The needle guide systems include both fixed and adjustable needle guides for use with a probe of the sonography device.

In one embodiment, the needle guide includes a needle guide body that is rotatably mounted to a sonography device probe. A plurality of needle channels is disposed on a surface of the needle guide body. Each needle channel can be selectively rotated into position to guide a needle into a body of a patient at a predetermined needle insertion angle. If another needle insertion angle is desired, the needle guide is rotated to place a new needle channel defining the desired needle insertion angle into position. The needle guide can be permanently or removably attached to the probe.

In another embodiment, a needle guide is disclosed and includes an extended guide feature, such as a guide cone, to assist in inserting a needle into the needle channel.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 7A-8F are various views of an adjustable needle guide system according to another embodiment;

FIGS. 9A-10F are various views of an adjustable needle guide system according to yet another embodiment;

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a needle or catheter placed within the body of a patient is considered a distal end of the needle or catheter, while the needle or catheter end remaining outside the body is a proximal end of the needle or catheter. Also, the words "including," "has," and "having," as used herein, including the claims, shall have the same meaning as the word "comprising."

FIGS. 1-11D depict various features of embodiments of the present invention, which are generally directed to needle guide systems for use with a sonographic imaging device in assisting the percutaneous insertion of a needle or other medical device into a body portion, such as a vasculature of a patient, for instance.

Figure 1:
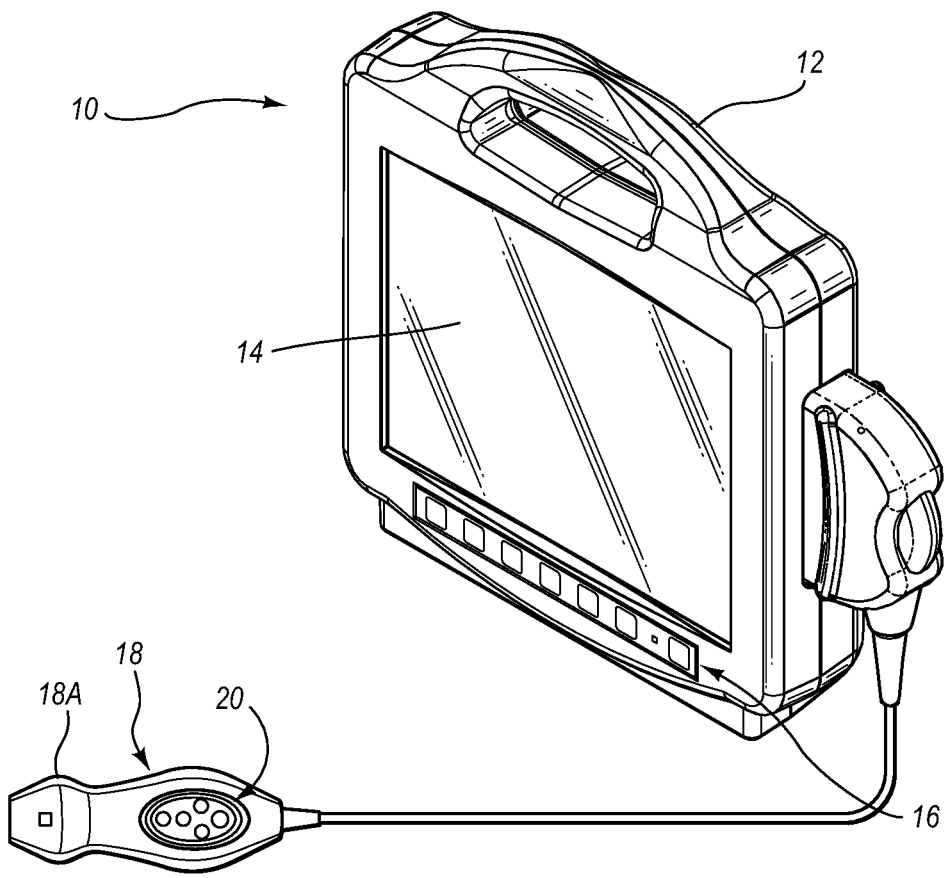
FIG. 1 is simplified perspective view of a sonographic imaging system that serves as an example environment in which embodiments of the present invention can be practiced.

Reference is first made to FIG. 1 in describing a sonographic imaging system ("system"), generally described at 10, for ultrasonically imaging portions of a patient body. The system 10 includes a console 12 including a display 14 and one or more user input controls 16. In one embodiment, the system 10 also includes a probe 18 including one or more user controls in the form of control buttons 20. Briefly, the probe 18 is configured to transmit ultrasonic signals from a head portion 18A thereof into a portion of a patient body and to receive the ultrasonic signals after reflection by internal structures of the patient body. The system 10 processes the reflected ultrasonic signals for depiction on the display 14.

The user input controls 16 of the console 12 may include, for example, image gain controls to adjust the amplification of a received ultrasonic signal, image depth controls to image structures at different depths and adjust the focus of an ultrasonic image displayed on the display 14, depth marker controls to selectively display depth markers and/or grid lines, print and/or save controls to print/save an image currently displayed on the display, image freeze controls to pause an image currently displayed on the display, time/date set controls, and other controls for operating the system 10. Corresponding controls, or a subset thereof, are also included in the control buttons 20 on the probe 18. In addition, in other embodiments the functionality of the user input controls 16 can be provided by a keyboard, mouse, or other suitable input device.

Figure 2:
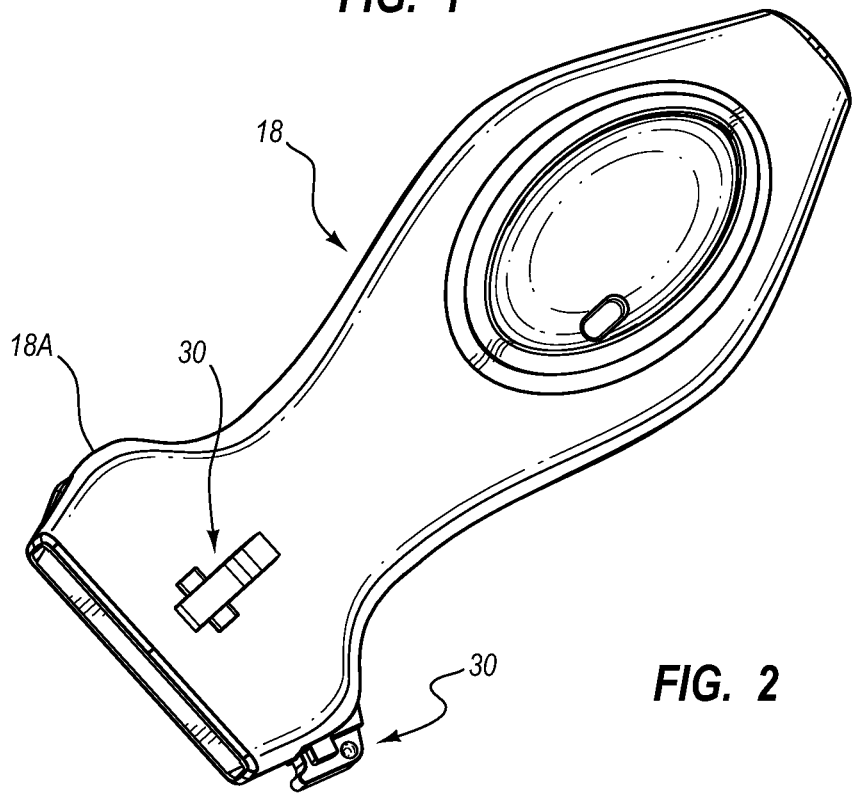
FIG. 2 is a perspective view of a handheld probe of the system of FIG. 1.

FIG. 2 shows the probe 18 of FIG. 1, including two needle guide connectors 30 that are included as part of a needle guide mounting system configured in accordance with one example embodiment. The needle guide connectors 30 are included on front and side portions of the probe 18 but are identically configured in the present embodiment. As such, the details of only one of the connectors will be described in detail here. It should be appreciated that in other embodiments the needle guide connectors may differ in size, configuration, the number included on the probe, etc. In addition, the design and configuration of the probe is merely one example of an ultrasonic probe that can benefit from the principles described herein.

Figure 3A:
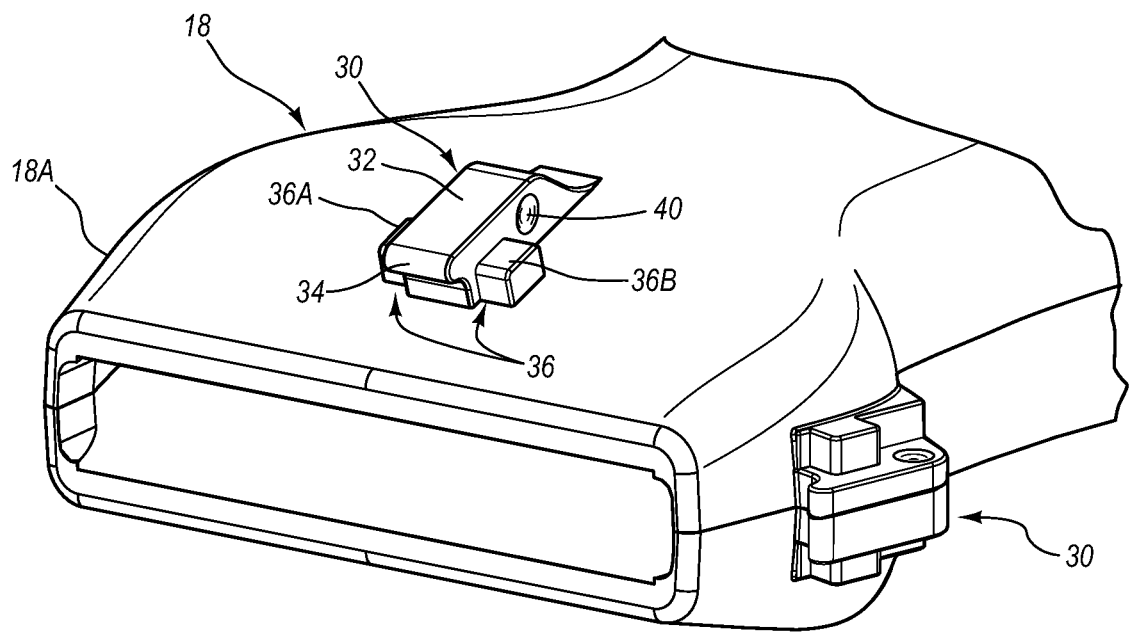
FIGS. 3A and 3B are various views of a portion of a needle guide system included on a handheld probe according to one example embodiment, included on the probe of FIG. 2.
Figure 3B:
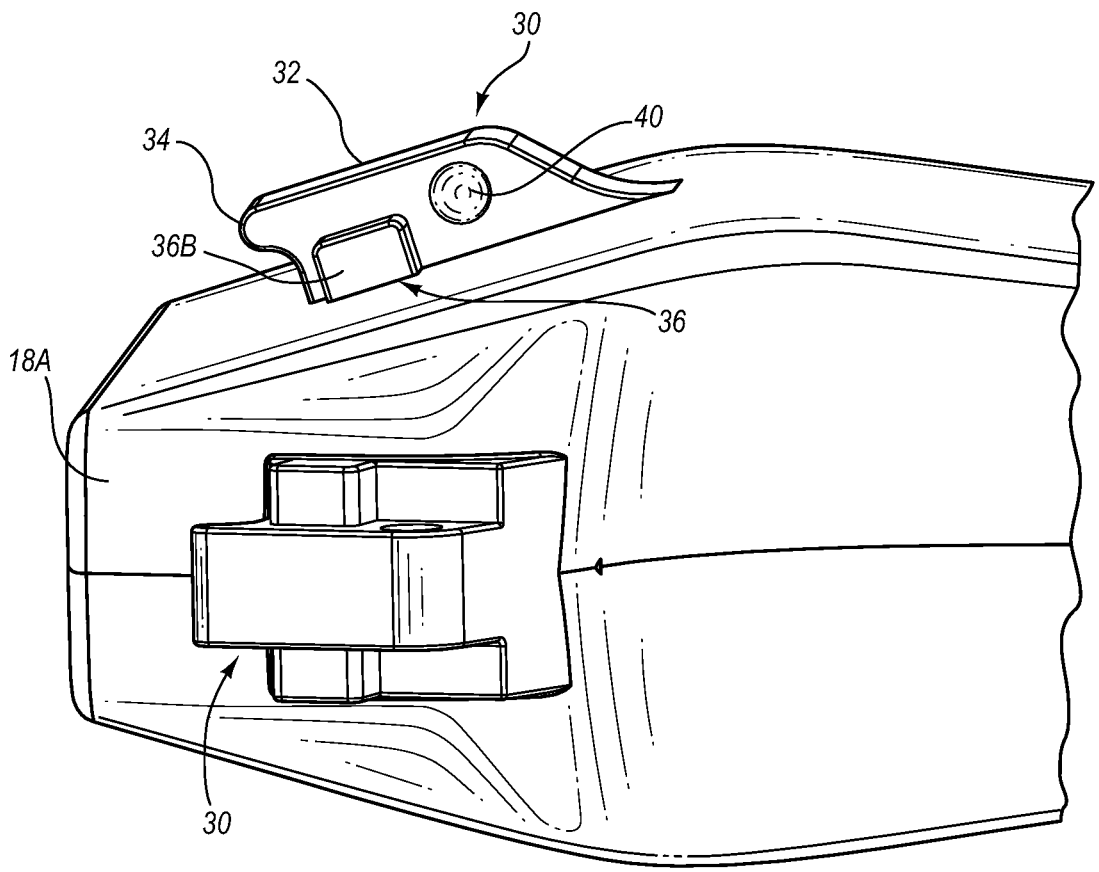

FIGS. 3A and 3B give further details of the needle guide connectors 30 according to one embodiment. Each connector 30 includes an elongate first mounting surface 32, extending from the surface of the probe head portion 18A, which is configured to receive a needle guide thereon, as will be described. An overhang 34 is defined at an end of the mounting surface 32 for assistance in maintaining engagement of the needle guide with the connector 30. A second mounting surface 36 is also included on the each connector 30, which surface defines two stability extensions 36A, 36B. In the present embodiment, the stability extensions 36A, 36B are integrally formed with the first mounting surface 32 and extend along an axis in a direction that is substantially orthogonal to a longitudinal axis of the first mounting surface. So configured, the second mounting surface 36, as defined by the stability extensions 36A and 36B, also extends substantially orthogonal to the first mounting surface 32, though in other embodiments the two mounting surfaces can be aligned at other angles with respect to one another. Note that the size, number, and orientation of the second mounting surface and its respective stability extensions with respect to the first mounting surface can vary from what is explicitly described herein.

One or more depressions 40 are defined on side surfaces of the first mounting surface 32 for engagement with corresponding protrusions defined on the needle guide, as will be described. Of course, other configurations for maintaining engagement between the needle guide and the mounting surfaces of the needle guide connector 30 can also be employed.

Reference is now made to FIGS. 4A-4D, which depict various details of a needle guide, generally designated at 50, in accordance with one example embodiment. As shown, the needle guide 50 includes a top surface 52 on which a needle channel 54, defined by two lips 55, is defined for guiding a needle to a body portion imaged by the system 10 via percutaneous insertion. The top surface 52, and therefore the needle channel 54, is angled with respect to a longitudinal axis of the probe 18 so as to enable the needle to intercept the targeted body portion at a depth as determined by the ultrasonic imaging performed by the system 10. The needle insertion angle defined by the needle channel 54 can vary according to the configuration of the needle guide. Thus, selection of an appropriately angled needle guide is determined by the depth of the intended subcutaneous target within the patient body to be intercepted. As such, the specific size and configuration details of the needle guide described herein are merely examples.

Figure 4A:
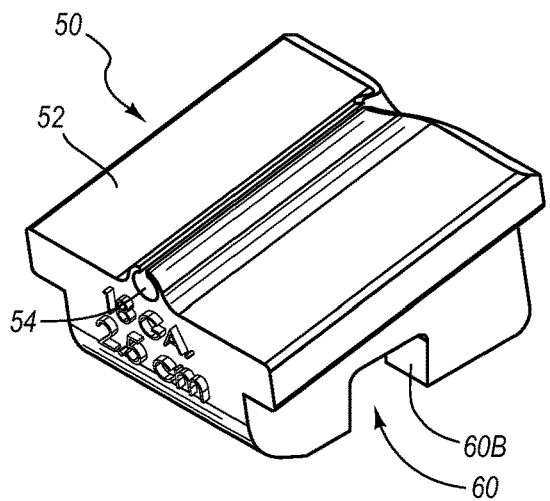
FIGS. 4A-4D are various views of a needle guide for use with the handheld probe shown in FIGS. 3A and 3B, according to one embodiment.
Figure 4B:
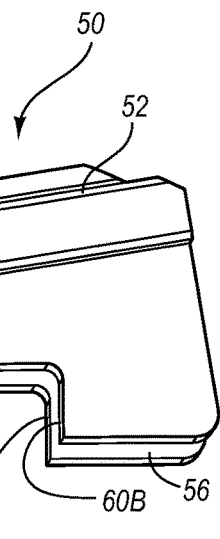
Figure 4C:
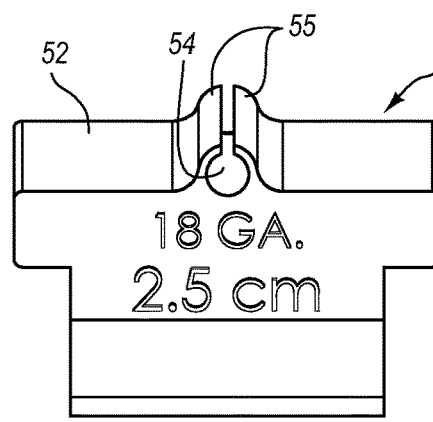
Figure 4D:
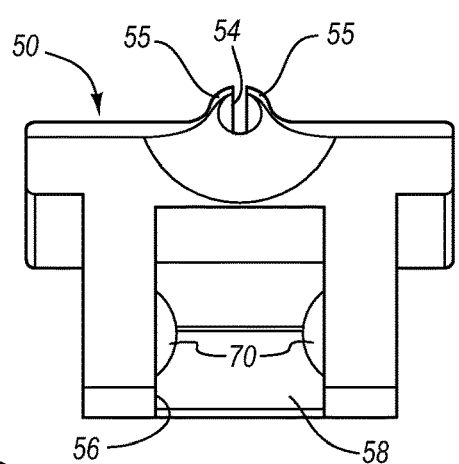

The needle guide 50 defines a first cavity 56, best seen in FIG. 4D, which is shaped to receive therein the first mounting surface 32 of the connector 30 when the needle guide is removably attached to the probe 18. A smoothly shaped extended surface 58 is included at the closed end of the cavity 56 and is configured for interfacing with the smoothly shaped overhang 34 of the first mounting surface 32 in retaining the needle guide 50 on the connector 30 when attached thereto. The extended surface 58 and overhang 34 can be configured in a variety of ways so as to assist in retaining the needle guide on the connector 30.

Figure 4E:
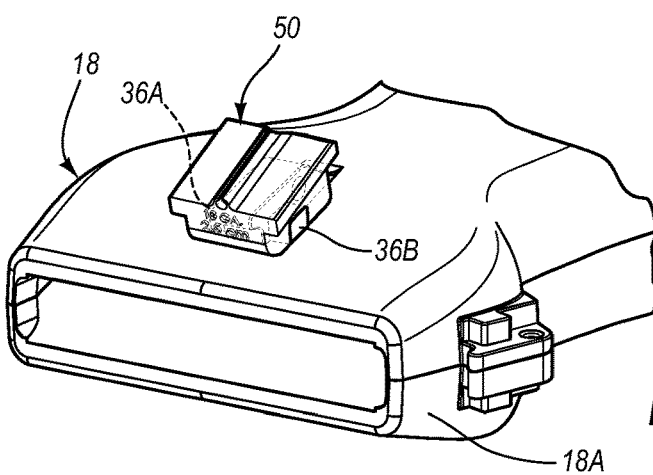
FIG. 4E is a perspective view of the needle guide of FIGS. 4A-4D attached to the probe of FIG. 2.

A second cavity 60, which crosses substantially orthogonally the first cavity 56 and includes notches 60A, 60B, is defined by the body of the needle guide 50, as best seen in FIG. 4B. The notches 60A, 60B of the second cavity 60 are positioned to respectively receive therein the stability extensions 36A, 36B when the needle guide 50 is attached to the needle guide connector 30, such as in a snap-fit configuration for instance, as shown in FIG. 4E. So attached, the stability extensions 36A, 36B of the connector 30 engage the notches 60A, 60B and this engagement, together with the engagement of the first mounting surface 32 with the needle guide cavity 56, secures the needle guide in place with respect to the probe 18. This in turn provides a stable needle guide structure that resists undesired movement, such as the needle guide undesirably slipping off the probe in a direction parallel to a longitudinal axis of the probe 18. Thus, the needle guide remains in place to enable a clinician to insert a needle or other medical instrument into the target area of the patient body via the needle channel 54 while the target area is imaged by the sonography system 10. It is appreciated that the angle of intersection between the first cavity 56 and the second cavity 60 of the needle guide 50 should be configured to match the angle of intersection between the first mounting surface 32 and the second mounting surface 36 of the needle guide connector 30 of the probe 18 in all cases, regardless of whether the angle of intersection is orthogonal.

The needle guide 50 further includes protrusions 70 in the first cavity 56 that are sized and positioned to engage with the depressions 40 (FIGS. 3A, 3B) of the needle guide connector 30 when the needle guide is attached to the needle guide connector 30. Note that the size, shape, number, and other configuration details of the needle guide cavities can vary from what is described herein while still residing within the scope of present embodiments. For instance, the shape defined by the notches 60A, 60B, can be triangular, rounded, etc., instead of the square configuration shown here.

The needle channel 54 of FIGS. 4A-4E is shown to be sized for an 18 Gauge needle. In other embodiments, however, the needle channel can be sized to accommodate needles of other sizes and configurations. Also, the needle guide can be configured in one embodiment to accept devices other than needles, such as trocars or catheters for instance. As mentioned above, the needle guide top surface can be configured such that the needle channel defines an angle with a longitudinal axis of the probe 18 different from what is shown in FIGS. 4A-4E. As such, multiple needle guides, each having a needle channel defining a unique angle with the longitudinal axis of the probe 18, can be constructed as to be selectively attachable to/removable from the probe needle guide connector 30 of the probe 18, enabling a plurality of needle insertion angles to be achieved with the system 10.

Figure 5A:
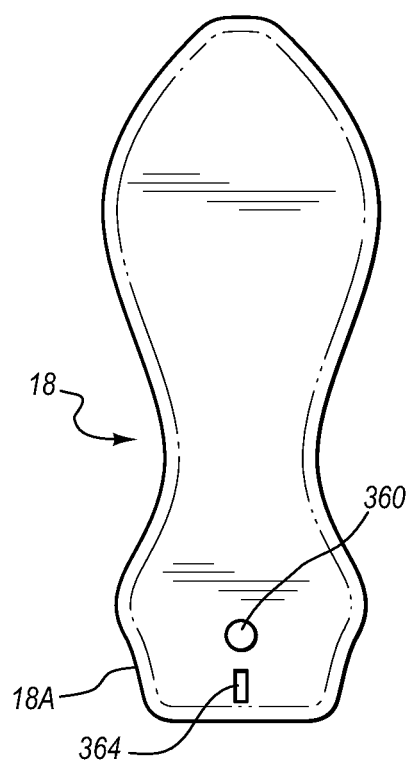
FIGS. 5A-6E are various views of an adjustable needle guide system according to one embodiment.

Reference is now made to FIGS. 5A-6E in describing a needle guide system according to another embodiment. FIGS. 5A and 5B show the probe 18 including a mounting component, such as a mounting ball 360, on the probe head portion 18A for rotatably receiving a rotatable needle guide 350, shown in FIGS. 6A and 6B. As shown, the needle guide 350 includes a circular body that defines a chamfered or slanted top surface 352. A plurality of needle channels 354 is included on the top surface. Each needle channel 354 is defined by two lips 455 or other suitable structure. The top surface 352 is configured such that each needle channel 354 is positioned at a unique angle. For instance, FIG. 6B shows one needle channel 354 of the needle guide 350 angled to define a deflection angle $\varphi_1$ with respect to horizontal and another needle channel 354 angled to define a deflection angle $\varphi_2$ with respect to horizontal, from the perspective shown in FIG. 6B. As will be seen, this enables the needle guide to guide a needle into the patient body at one of a plurality of different needle insertion angles, measured with respect to a longitudinal axis of the probe 18 to which the needle guide is either removably or permanently attached. In the illustrated embodiment, five needle channels 354 are included on the top surface 352 of the needle guide 350, though more or fewer than this can be included. Also, though shown distributed in a star pattern, the distribution of the needle channels on the needle guide top surface can vary from what is shown and described herein.

Figure 5B:
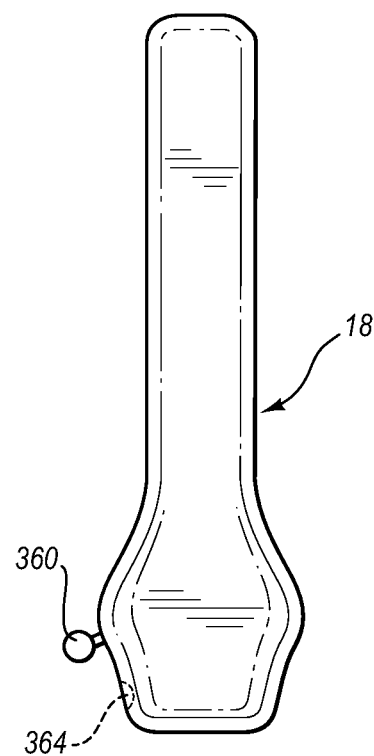
Figure 6A:
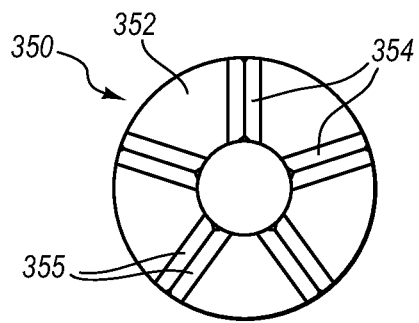
Figure 6B:
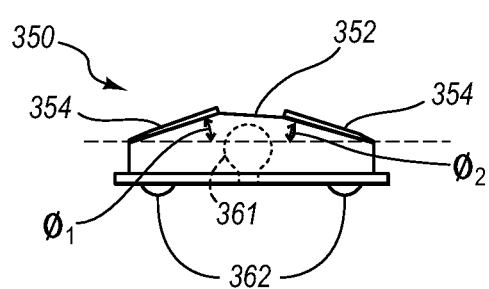
Figure 6C:
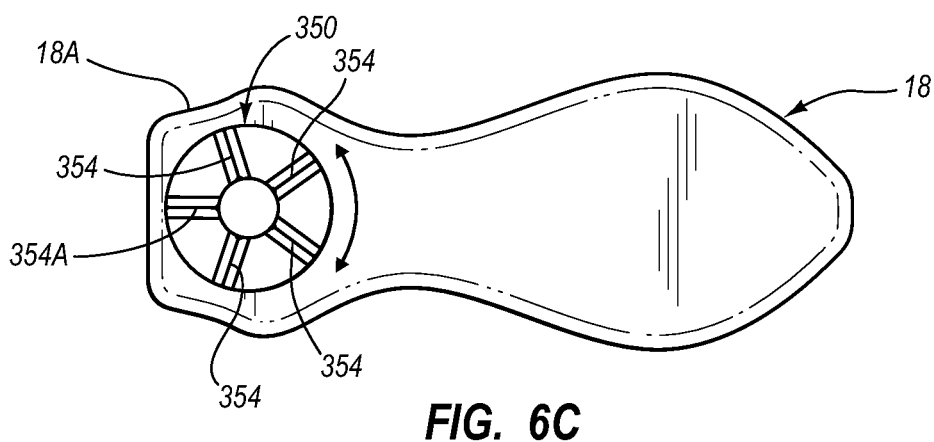

As mentioned, the needle guide 350 is configured to attach to a fixture on the probe 18, such as the mounting ball 360 shown in FIGS. 5A and 5B or other suitable structure, such that the needle guide 350 is rotatable with respect to the probe. The fixture can be placed on any suitable surface of the probe 18. One or more protrusions 362 are included on a bottom surface of the needle guide 350 and are each positioned so as to engage a depression 364 defined on the surface of the probe head portion 18A and thus secure the needle guide in a particular position until moved by a force sufficient to overcome the friction engagement between the corresponding protrusion and the depression. So configured, a clinician may rotate the needle guide 350, as shown in FIG. 6C, until the desired needle channel 354 having the desired insertion angle is aligned at a usable position 354A to enable the clinician to insert a correspondingly sized needle into the patient body via the selected needle channel to intercept an imaged target area of the patient body at a predetermined depth. Note that the location, number, and configuration of the protrusions and depressions can vary from what is shown and described.

Figure 6D:
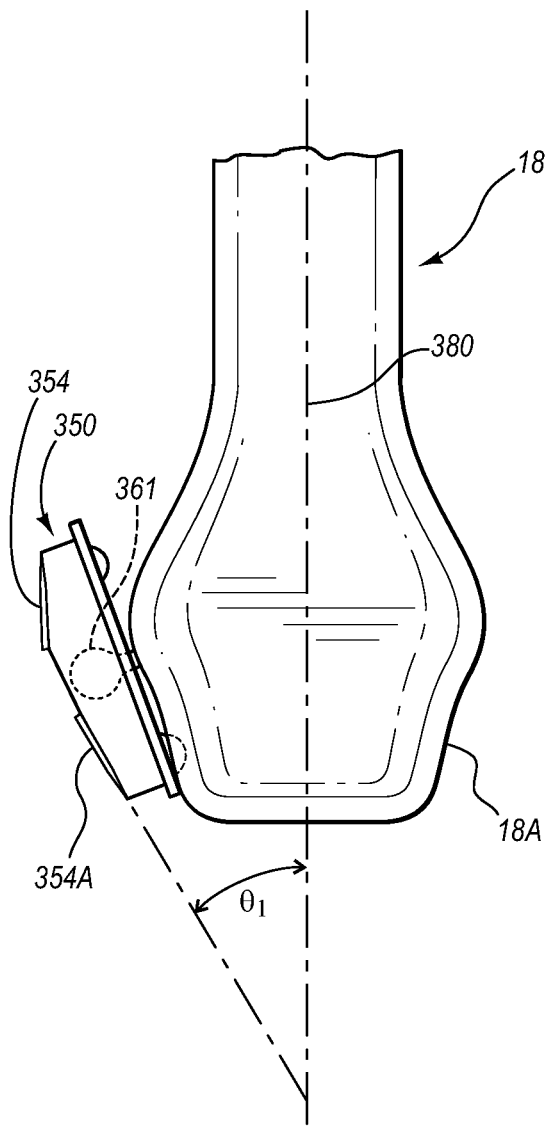
Figure 6E:
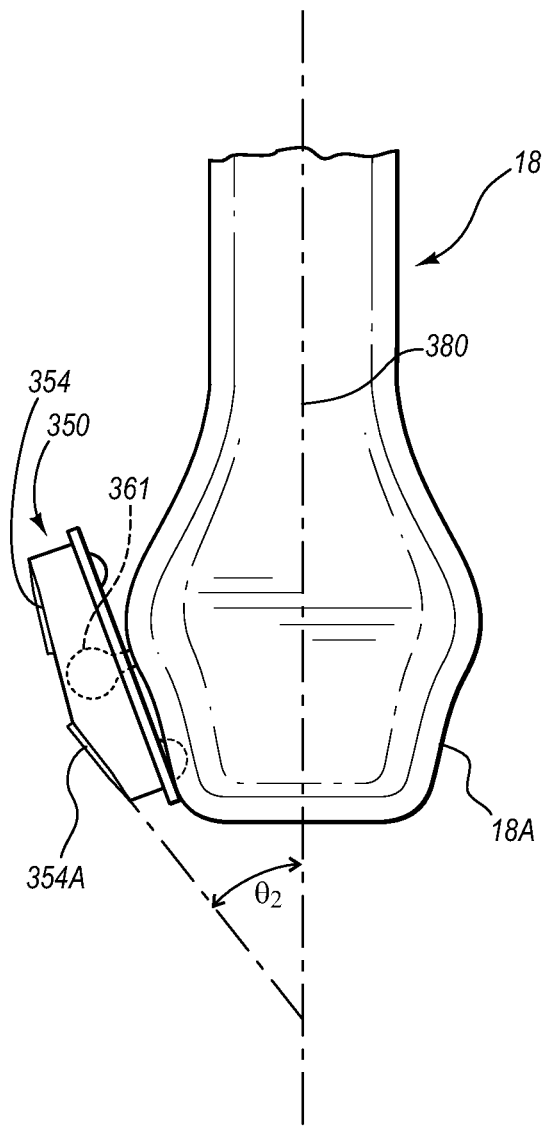

FIGS. 6D and 6E show how the needle guide 350 enables needle insertions of different angles of entry into the patient body. In FIG. 6D, one of the needle channels 354 is positioned for use, i.e., in the position 354A (see FIG. 6C) such that it defines a needle insertion angle $\theta_1$ with the longitudinal axis 380 of the probe 18. In contrast, FIG. 6E shows another needle guide channel 354 in the position 354A, which defines a needle insertion angle $\theta_2$ with the probe longitudinal axis 380. As can be seen from FIGS. 6D and 6E, the needle path enabled by the needle channel 354 of FIG. 6D penetrates more deeply relative to the needle path enabled by the needle channel 354 of FIG. 6E. As such, the needle channel 354 of FIG. 6D can be employed in order to enable a needle to intercept a target area of the patient body that is relatively deeper, while the needle channel shown in FIG. 6E can be employed to intercept a relatively shallower target area.

Thus, in accordance with the present embodiment, the needle guide 350 can be used to direct a needle to a proper depth within the patient body during use of the probe 18 and system 10. In particular, once a target area of the patient body has been located by the probe 18 and imaged by the system 10, the clinician rotates the needle guide 350 until a desired one of the needle channels 354 having a desired needle insertion angle with respect to the longitudinal axis 380 of the probe 18 is in the position 354A and ready for use. The clinician can then insert the needle into the needle channel 354, which channel guides the needle into the patient body at the desired needle insertion angle until the needle intercepts the target area.

Note that the shape and size of the needle guide can vary from what is described here. For instance, the general shape of the needle guide can be hexagonal, pentagonal, triangular, square, or other geometric shape in one embodiment. Also, the needle guide can be reduced in size from what is shown in FIGS. 6D and 6E in order to match a configuration of the sonographic probe. The needle channels can each be sized to accommodate needles of differing gauges in one embodiment.

Reference is now made to FIGS. 7A-8E in describing a needle guide system according to another embodiment. In particular, FIGS. 8A-8E show a needle guide 450, which generally includes a base 452 and a flexible extension 460. The base 452 includes on a top surface thereof a needle channel 454 defined by lips 455 and on a bottom surface a connector 456 for attaching the needle guide 450 to the probe 18 and longitudinally extending stability rails 458 for preventing twisting or torsion of the needle guide during use on the probe. The flexible extension 460 is an elongate member that longitudinally extends from the base 452 and includes a first engagement feature, such as a hook 462, at a free end 460A of the extension.

Figures 7A, 7B:
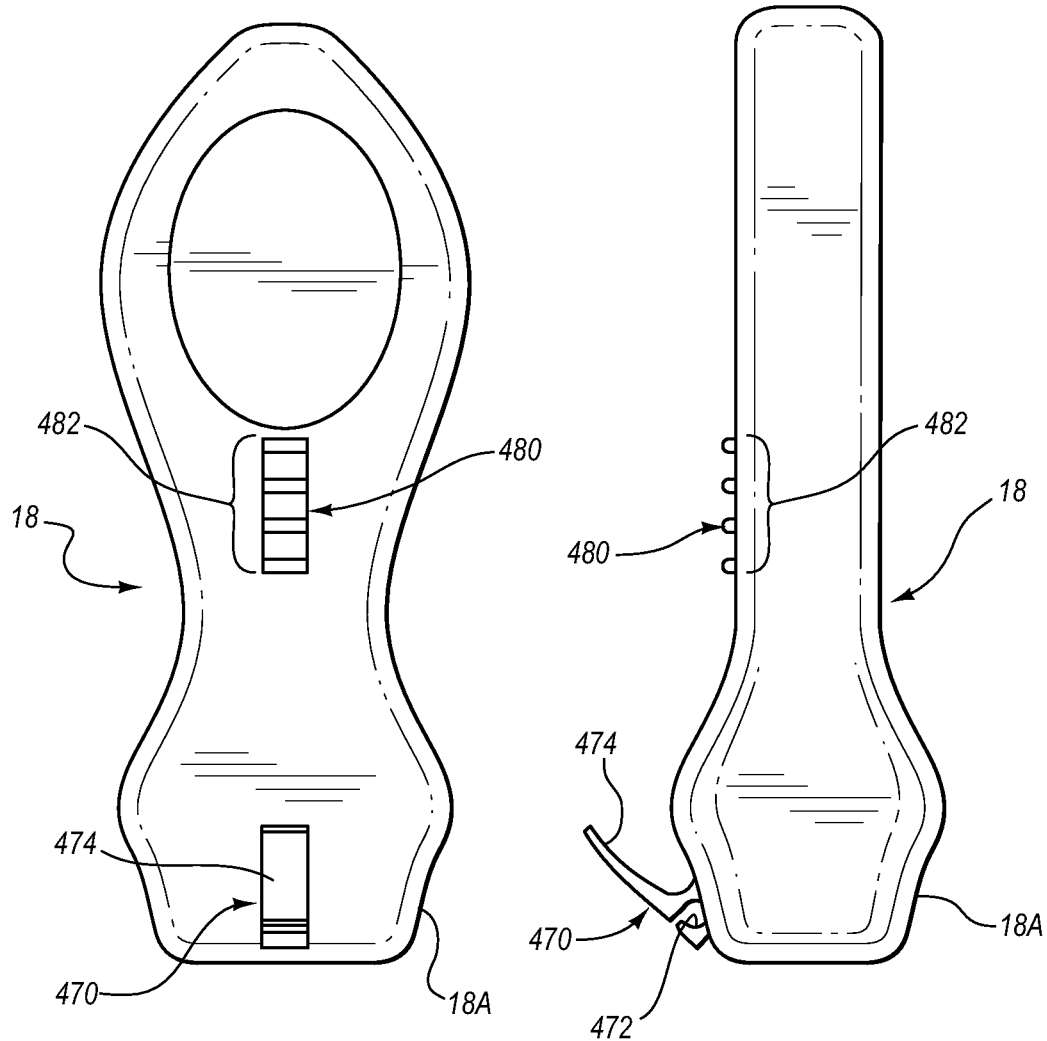
Figure 8F:
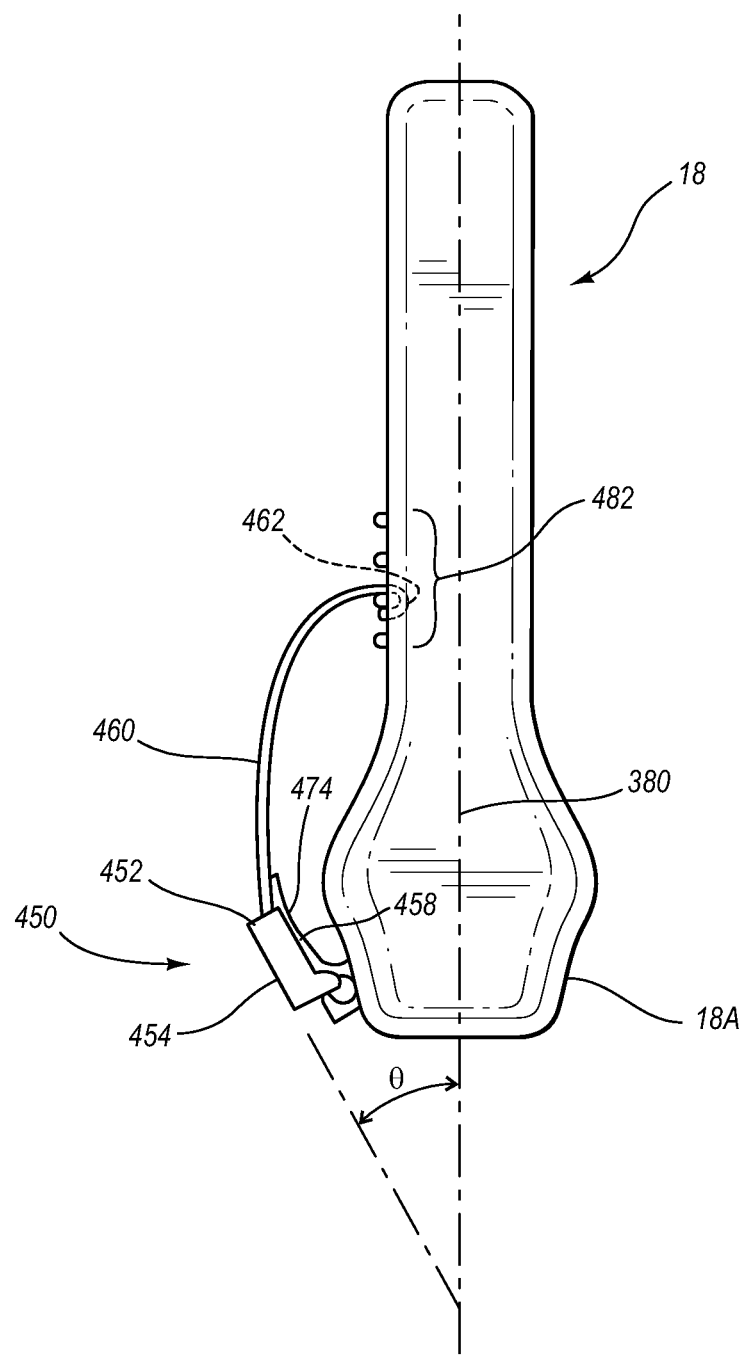

As shown in FIGS. 7A and 7B, in the present embodiment the probe 18 includes on its head portion 18A a connector 470 to which the needle guide can removably attach. The connector 470, which itself can be removably or permanently attached to the probe 18, includes a cavity 472 for receiving the connector 456 of the needle guide base 452, and a support arm 474 proximally extending at an acute angle from the probe surface. The probe 18 further includes a receiver array 480, which includes a second engagement feature, configured here as a plurality of spaced apart bars 482 with which the needle guide hook 462 can engage, as shown in FIG. 8F, for example. Specifically, FIG. 8F shows the needle guide 450 attached to the probe 18 via engagement of its connector 456 with the cavity 472 of the probe connector 470. The hook 462 of the needle guide flexible extension 460 is shown engaged with one of the hook receiving bars 482 of the receiver array 480, thus creating an attachment between the first engagement feature of the needle guide, i.e., the hook 462, and the second engagement feature of the probe, i.e., one of the bars 482.

So configured, the needle channel 454 of the needle guide is oriented to define a needle insertion angle θ with the probe longitudinal axis 380. Note that the extension 460 is configured to be flexible enough to allow for the bending thereof as shown in FIG. 8F. The support arm 474 in the current embodiment is resilient while also providing the needed rigidity for the needle guide base 452 so as to maintain the needle channel 454 in a substantially fixed location after the angle of the needle guide 450 has been selected and set. Additionally, the stability rails 458 straddle the support arm 474 to prevent undesired twisting or torsion of the needle guide 450 during use.

Should it be desired to change the needle insertion angle defined by the needle channel 454, the hook 462 can be manually moved to engage another of the bars 482 of the probe receiver array 480. This in turn alters the needle insertion angle and the depth to which the needle will be inserted into the patient body by the clinician. Generally, in the present embodiment movement of the hook 462 to more proximal bars 482 lessens the needle insertion angle, which in turn enables the needle to penetrate to a relatively deeper target area in the patient body. Of course, the needle guide system can be configured such that a different relationship exists between movement of the needle guide components and the needle insertion angle. Indeed, in one embodiment the adjustable engagement feature can be included on the needle guide itself instead of on the probe, as is the case with the embodiment described here.

FIGS. 9A-9E depict a variation of the needle guide 450, wherein the free end 460A of the flexible extension 460 serves as a first engagement feature of the needle guide in contrast to the hook of the previous embodiment, and wherein a receiver array 580 on the probe 18 (FIG. 10A) includes a second engagement feature implemented as a plurality of slots 582 instead of the bars of the previous embodiment. Further, the needle guide 450 shown in FIGS. 9A-9E is designed for use with a probe connector that includes no support arm, such as the support arm 474 shown in FIGS. 7A-8F. Instead, the flexible extension 460 in the present embodiment is configured so as to be more rigid, relative to the flexible extension of the embodiment depicted in FIGS. 7A-8F, thus enabling it to bend to engage the receiver array 580 while maintaining the needle guide base 452 at a desired position.

Figure 10A:
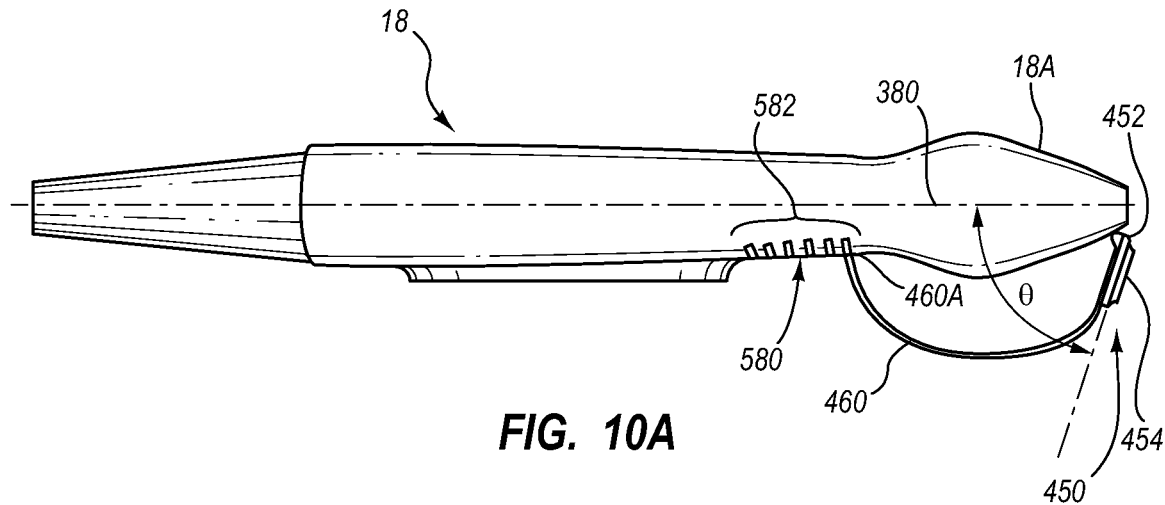
Figure 10B:
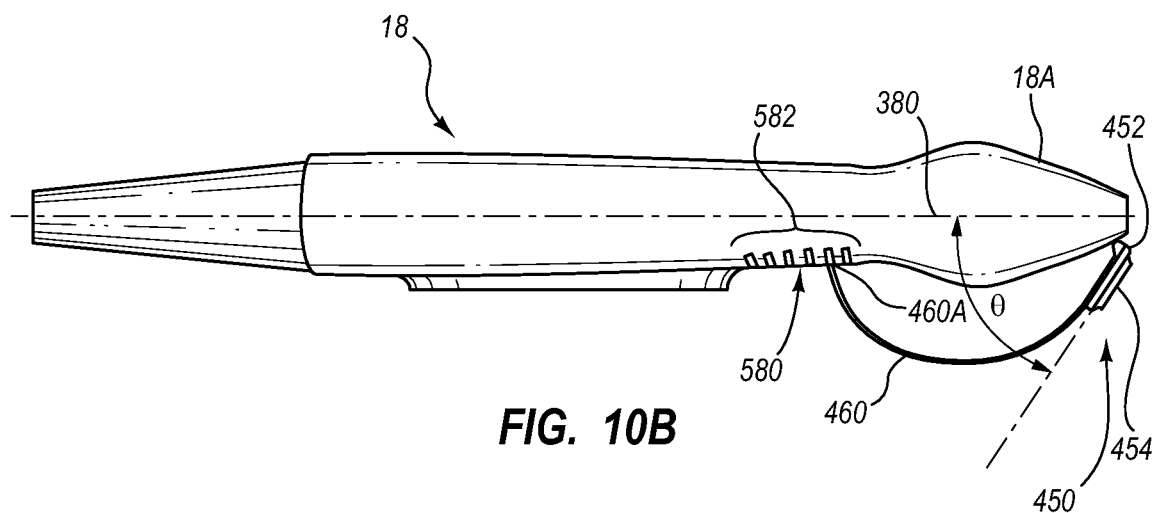
Figure 10C:
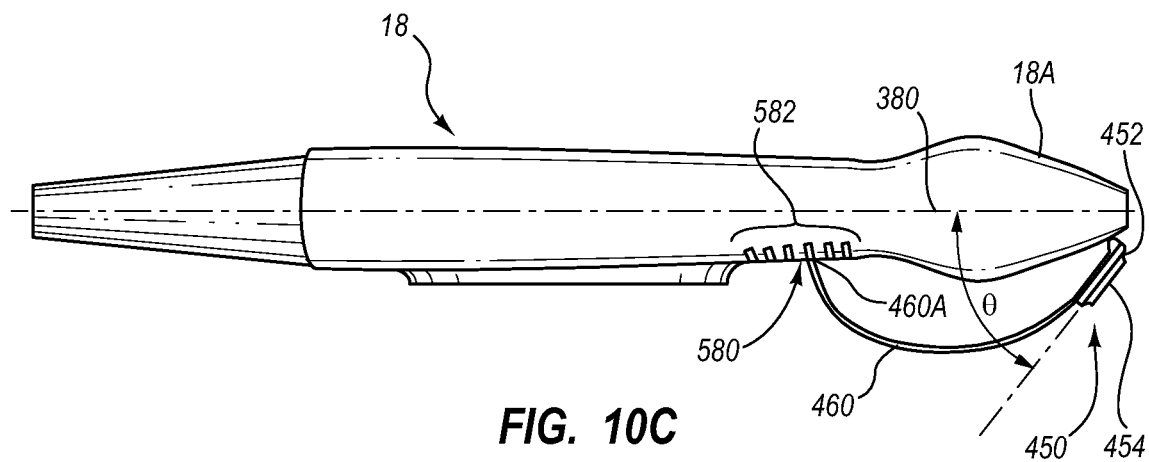
Figure 10D:
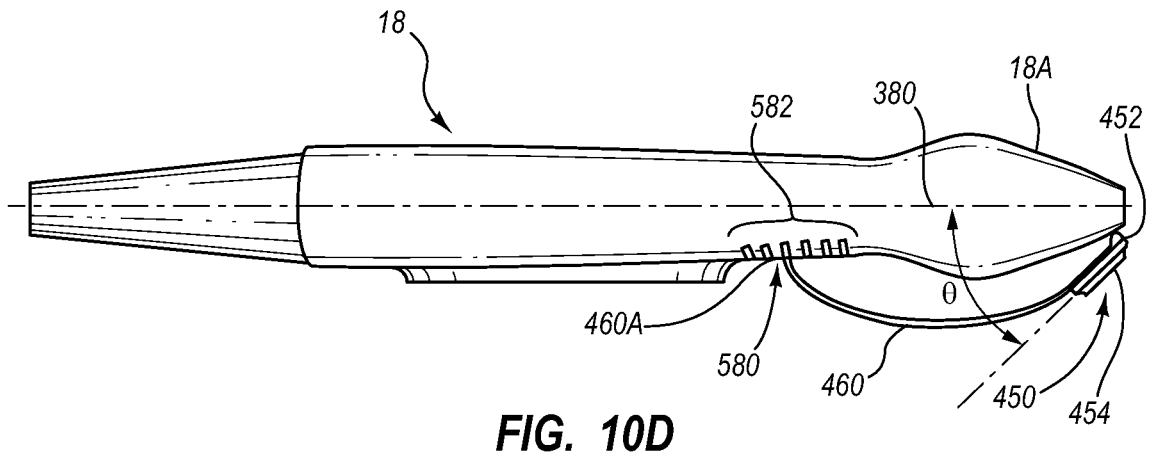
Figure 10E:
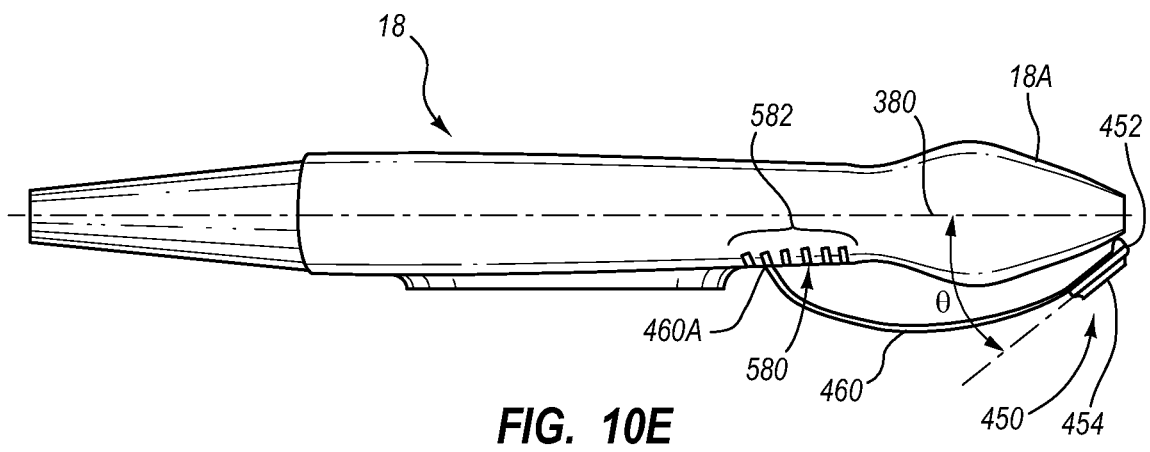
Figure 10F:
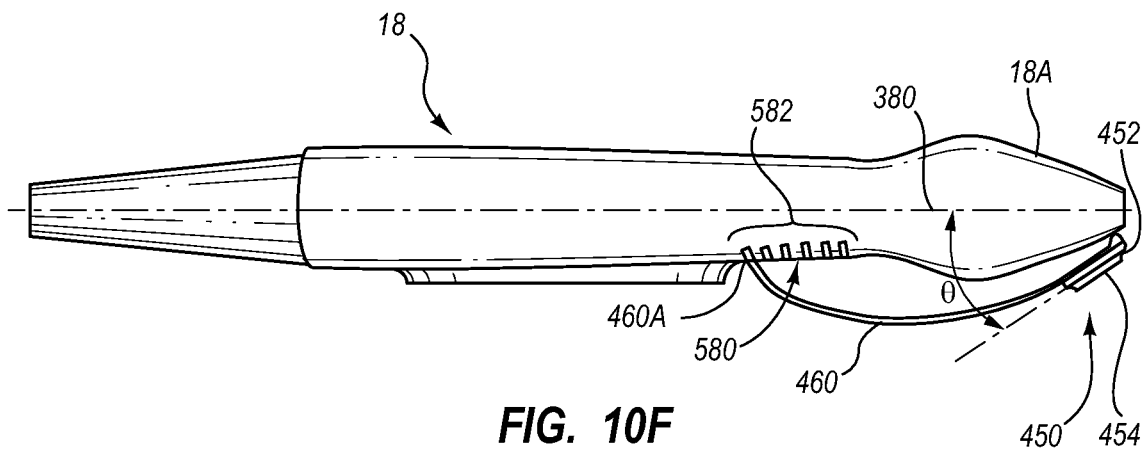

In greater detail, FIGS. 10A-10F show the manner of engagement of the needle guide 450 with the probe 18, according to the first and second engagement features just described above in connection with FIGS. 9A-9E. Note that in FIGS. 10A-10F, the probe connector for attachment of the needle guide has been removed for clarity. In particular, FIG. 10A shows the flexible extension 460 positioned such that the free end 460A thereof is received into the distal-most slot 582 of the probe receiver array 580. This causes the needle guide base 452 and the needle channel 454 disposed thereon to be positioned such that the needle channel defines a relatively large needle insertion angle θ with respect to the probe longitudinal axis 380, which corresponds to inserting a needle in a relatively superficial target area of the patient body located proximate the skin surface thereof.

FIGS. 10B-10F show that as the flexible extension free end 460A of the needle guide 450 is inserted into progressively more proximal slots 582 of the probe receiver array 580, the needle insertion angle θ is reduced, which corresponds to directing the needle to progressively deeper target areas of the patient body. As such, the slots 582 and needle guide 450 can be configured so as to position the needle channel 454 to define predetermined needle insertion angles. In one embodiment, for example, the needle guide system as described in connection with FIGS. 9A-10F can define needle insertion angles ranging from about three degrees to about 43 degrees, though it is appreciated that a variety of possible angles can be achieved. It is noted that the first and second engagement features of the needle guide and probe that are used to interconnect the two can vary from what is described herein, as appreciated by one skilled in the art.

Figure 11A:
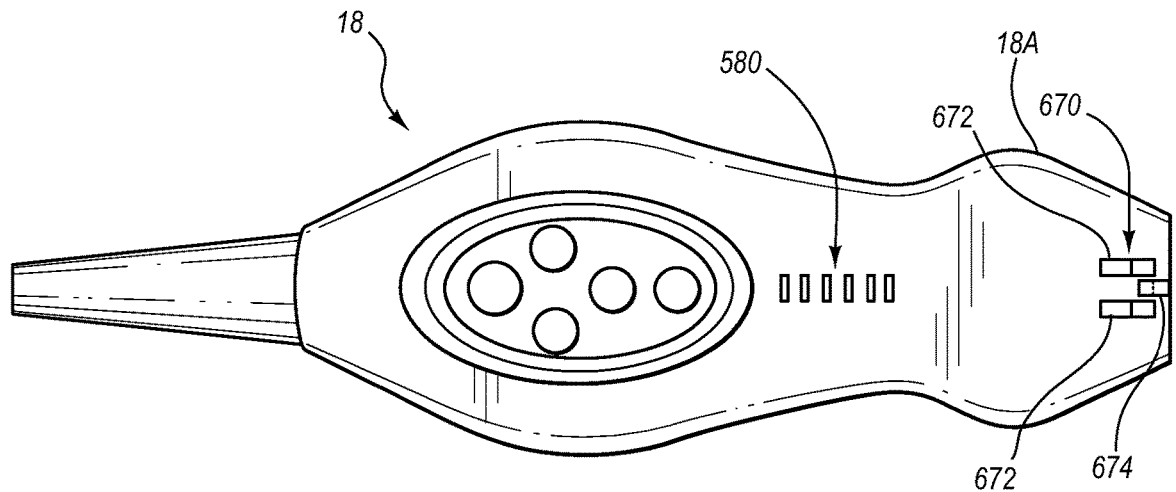
FIGS. 11A-11D show additional details of a needle guide system according to one embodiment.
Figure 11B:
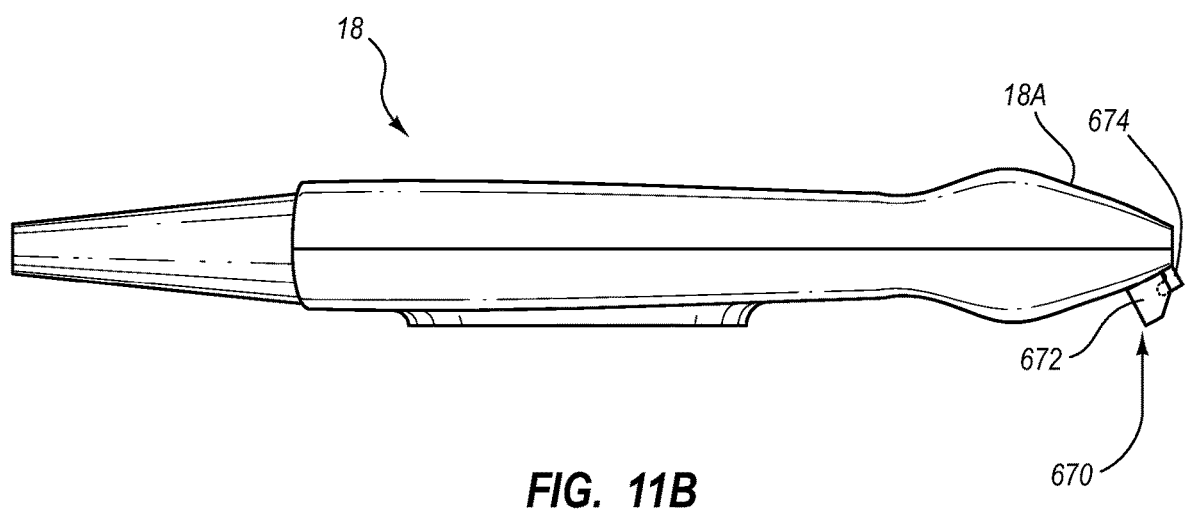
Figure 11C:
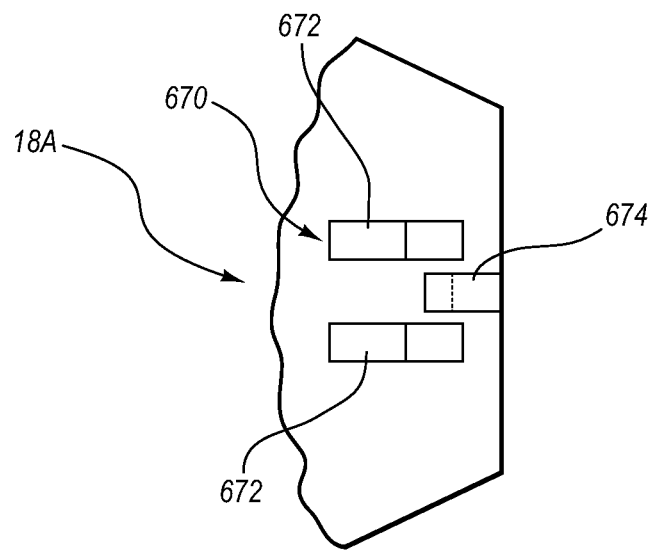
Figure 11D:
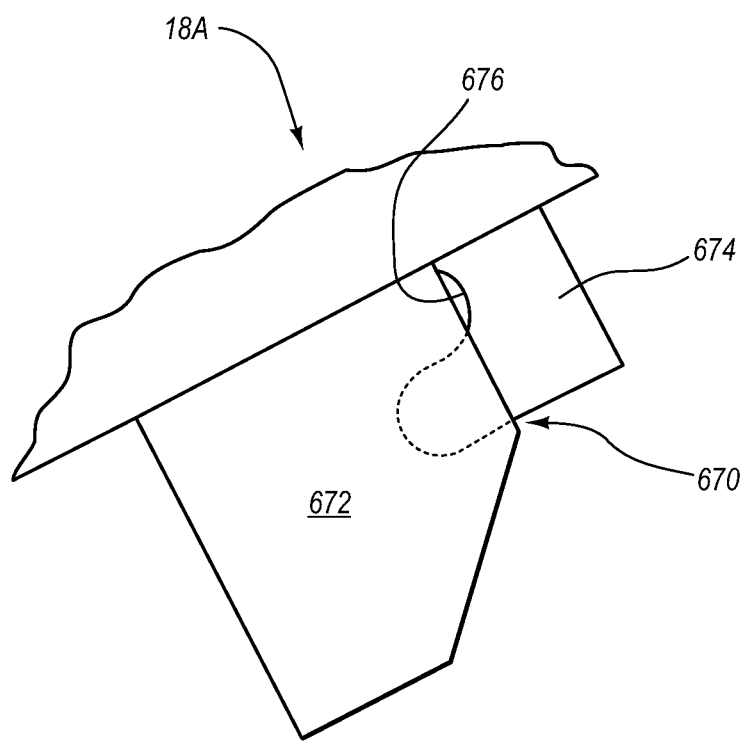

FIGS. 11A-11D depict one possible connector 670 for the probe head portion 18A for engaging a needle guide, according to one embodiment. In particular, the connector 670 includes two outer fins 672 in between which an inner fin 674 is positioned. As best seen in FIG. 11D, a recess 676 is included on the inner fin 674, and the outer fins 672, the inner fin 674, or all the fins include a resilient material so as to enable deformation thereof so as to facilitate insertion into the recess of a connector portion of the needle guide, such as the connector 456 of the needle guide 450 described in the embodiment associated with FIGS. 7A-8F, for example. In one embodiment, only the inner fin is resilient, while the outer fins are substantially rigid. It should therefore be appreciated that the manner of attachment between the needle guide and the probe can include any one of a number of possible designs. Also, it is appreciated that the needle channel can be defined in any one of a number of ways, in addition to the lips explicitly shown and described herein.

Figure 12:
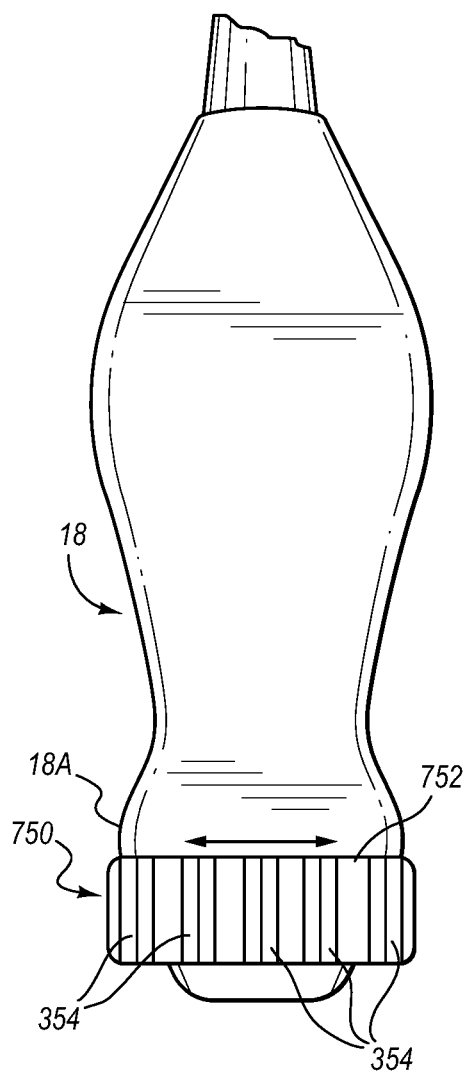
FIG. 12 is a top view of an adjustable needle guide system according to one another embodiment.
Figure 13:
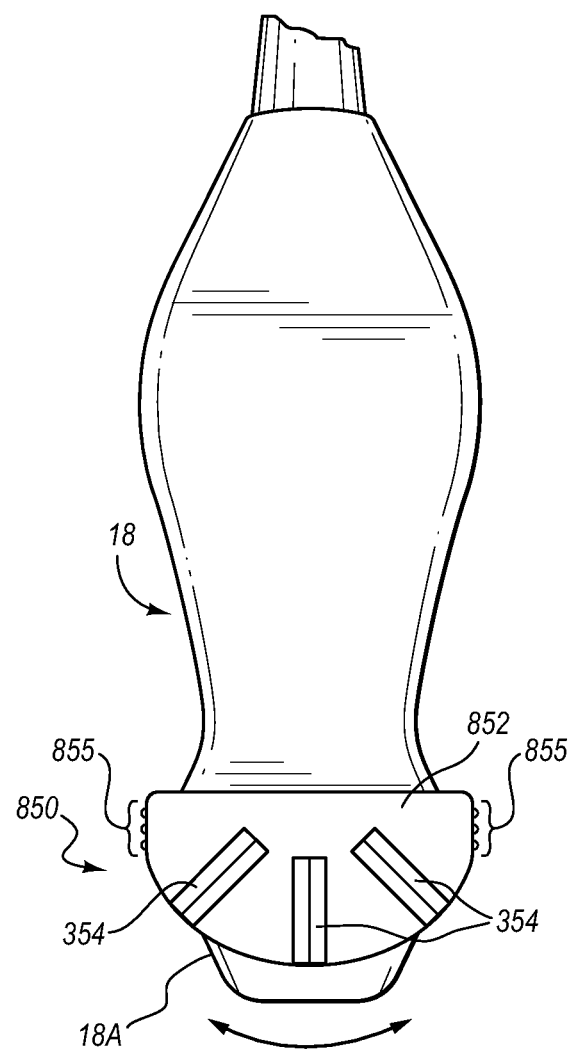
FIG. 13 is a top view of an adjustable needle guide system according to yet another embodiment.

FIGS. 12 and 13 depict yet other needle guide embodiments. In FIG. 12, a linear needle guide 750 is shown, including a top surface 752 on which are disposed a plurality of needle channels 354 that are each aligned to define differing needle insertion angles. A particular needle channel can be selected for use by laterally sliding the needle guide 750 as shown in FIG. 12. In FIG. 13, a semi-circular needle guide 850 is shown, including a top surface 852 on which a plurality of needle channels 354 are disposed in a fan pattern, each needle channel defining a different needle insertion angle. Finger grips 855 can be included on the body of the needle guide 850 to assist with movement of thereof to position a desired needle channel for use. These embodiments are therefore illustrative of the many different needle guide configurations possible.

Figure 14A:
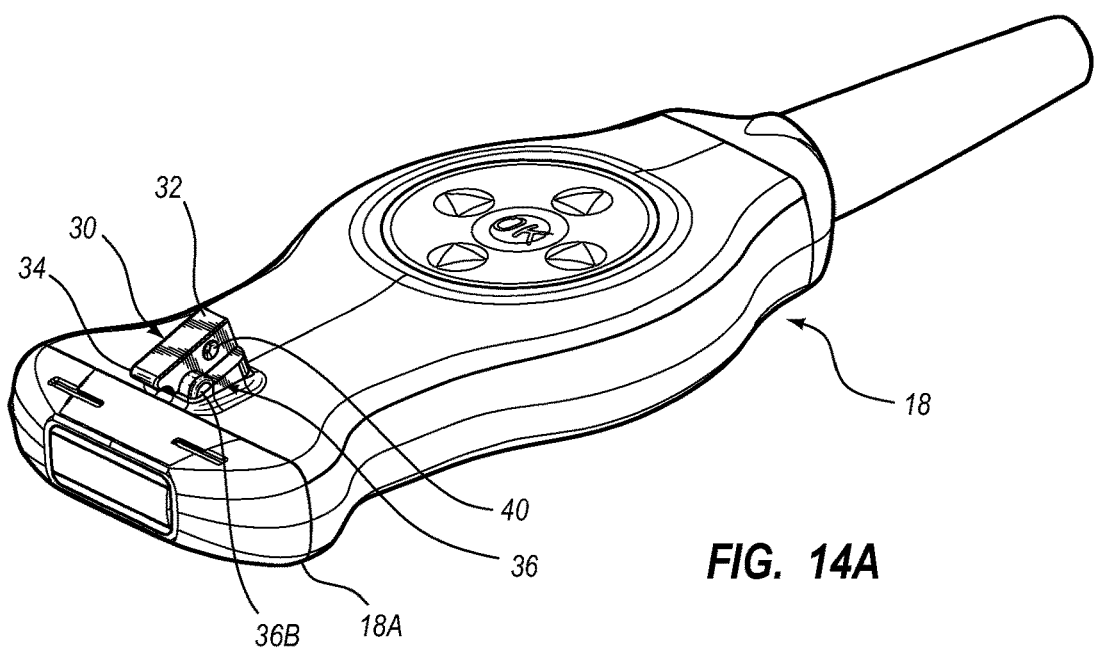
FIGS. 14A-14C show various views of a connector included on an ultrasound probe.

FIGS. 14A-16 depict various details of a needle guide/connector system for use with a probe, such as an ultrasound probe, according to one embodiment. In particular, FIGS. 14A-14C depict various details of the connector 30 included on the head portion 18A of the probe 18, according to the present embodiment. As the embodiment of FIGS. 14A-14C shares some similarity with the connector shown in FIGS. 3A and 3B, only selected aspects of the present connector 30 will be discussed.

Figure 14B:
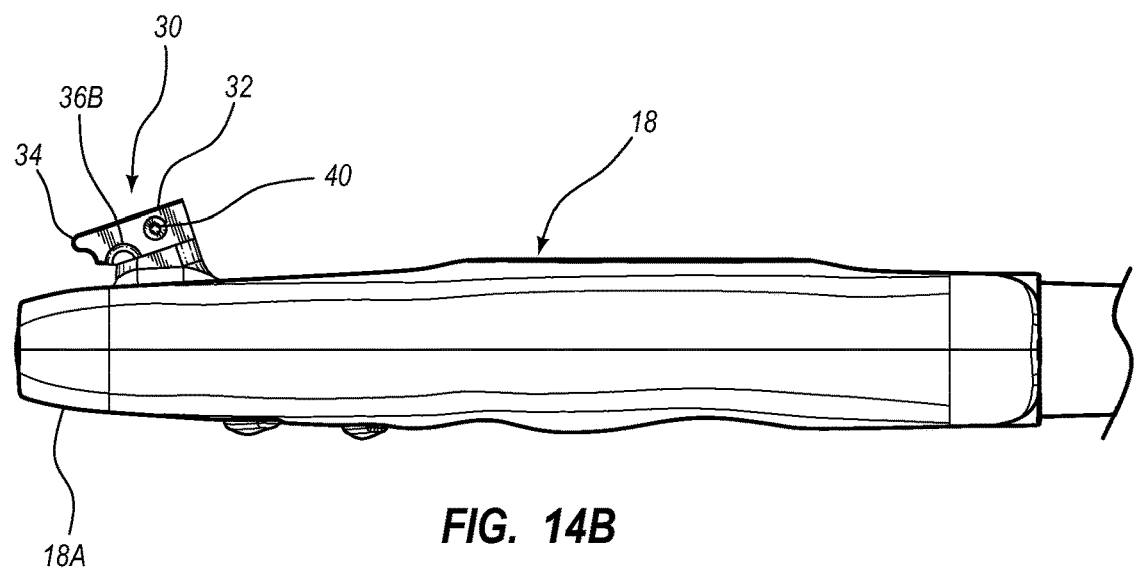
Figure 14C:
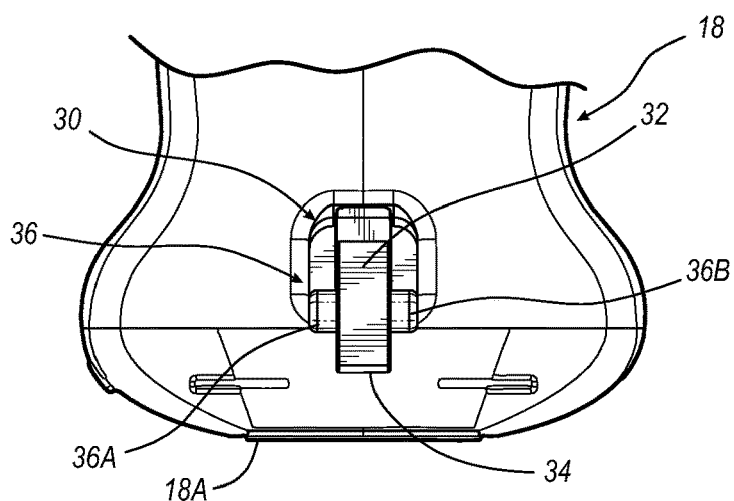

As shown in FIGS. 14A-14C, the connector 30 includes the first mounting surface 32 that terminates in the overhang 34. The second mounting surface 36 is also depicted, including the extensions 36A and 36B, for providing stability to a needle guide attached to the connector 30, as will be discussed further below. In contrast to the embodiment of the connector of FIGS. 3A and 3B, the extensions 36A and 36B here define a rounded shape. As mentioned, other extension shapes are possible. The depressions 40 are provided on either side of the connector 30, as before. The particular position of the connector 30, and its particular design, can vary from what is shown and described herein.

FIGS. 15A-15F depict various details of the needle guide 50 for use with the connector 30 of FIGS. 14A-14C, according to one embodiment. As the present embodiment shares some similarity with the needle guide shown in FIGS. 3A and 3B, only selected aspects of the present needle guide 50 will be discussed.

Note that the needle guides to be described in the following embodiments herein are configured so as to ease insertion of the needle into a guide channel of the needle guide. This facilitates ease of needle insertion even when the needle guide is positioned relatively far away from the user, such as is the case when the needle guide is included with a probe of an ultrasound imaging system and it is necessary to maintain the probe on the skin surface of the patient during loading of the needle into the needle guide. This circumstance arises, for instance, when the ultrasound imaging system includes a magnetic-based needle insertion guidance system, which often requires the ultrasound probe and attached needle guide to remain on the skin of the patient after magnetic calibration of the guidance system. Further details regarding an example of a magnetic-based needle insertion guidance system can be found in U.S. Pat. No. 10,524,691, filed Sep. 27, 2013, and titled "Needle Assembly Including an Aligned Magnetic Element," which is incorporated herein by reference in its entirety.

In light of the above, FIGS. 15A-15F depict various details of the needle guide 50, configured for removable attachment to the connector 30 of FIGS. 14A-14C or other portion of the ultrasound probe 18, in accordance with the present embodiment. As shown, the needle guide 50 includes the top surface 52 supported by one or more legs 53. The top surface 52 serves as the platform on which the needle channel 54—defined by two opposing, elongate lips 55 with a slot 55A interposed therebetween—is included for guiding a needle to a body portion imaged by the ultrasound imaging system 10 via percutaneous insertion. When the needle guide 50 is attached to the probe, the top surface 52, and therefore the needle channel 54, is angled with respect to a longitudinal axis of the probe 18 so as to enable the needle to intercept the targeted body portion at a depth as determined by the ultrasonic imaging performed by the system 10. The needle insertion angle defined by the needle channel 54 can vary according to the configuration of the needle guide.

Figure 15A:
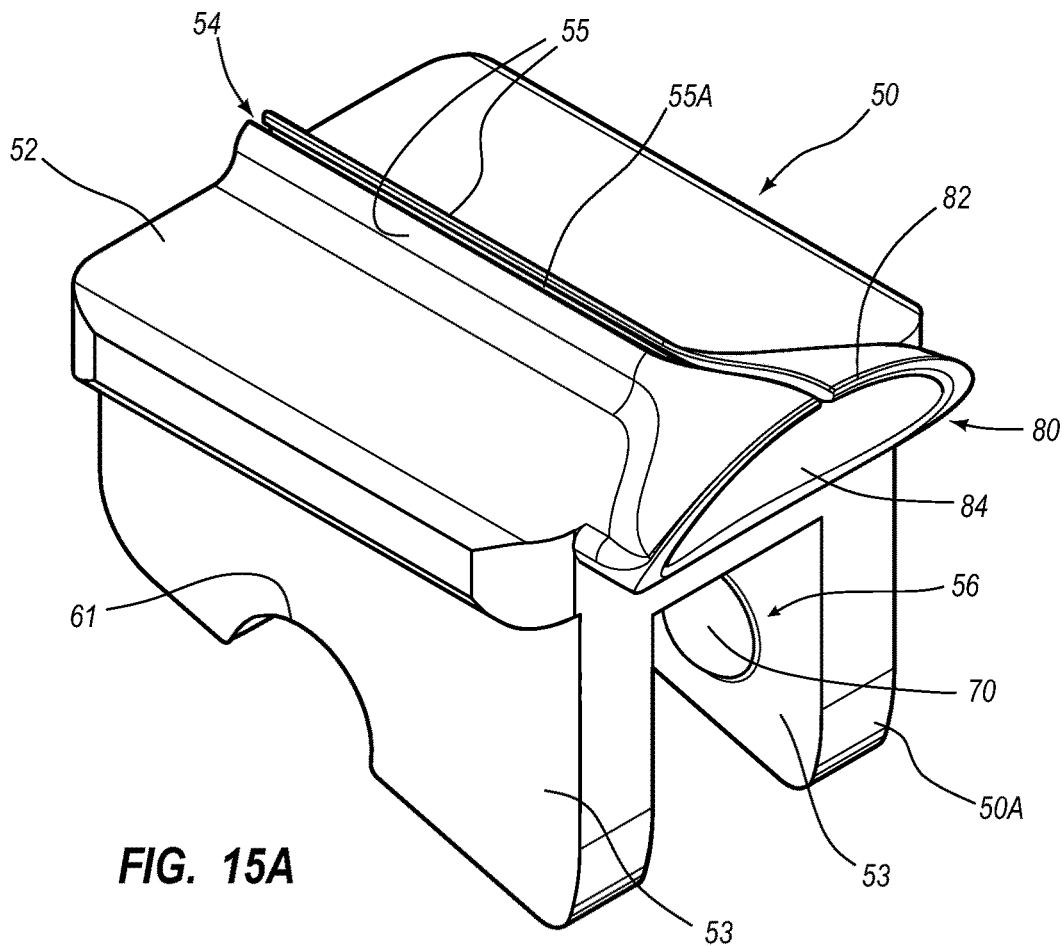
FIGS. 15A-15F show various views of a needle guide according to one embodiment.
Figure 15B:
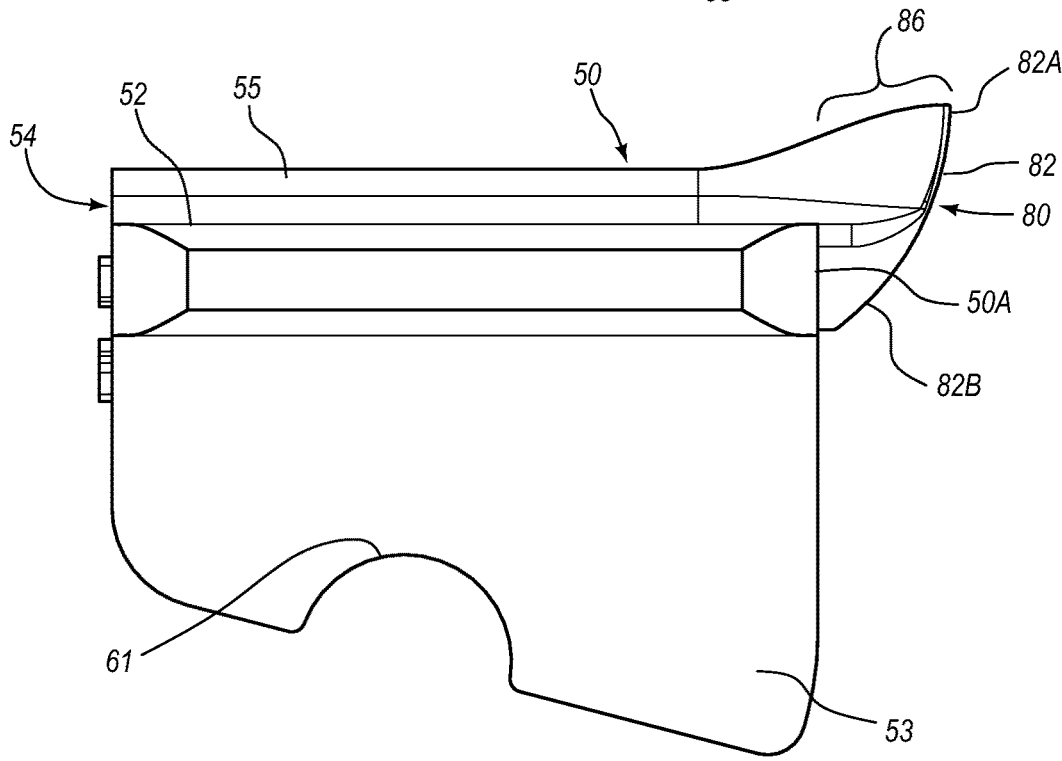
Figure 15C:
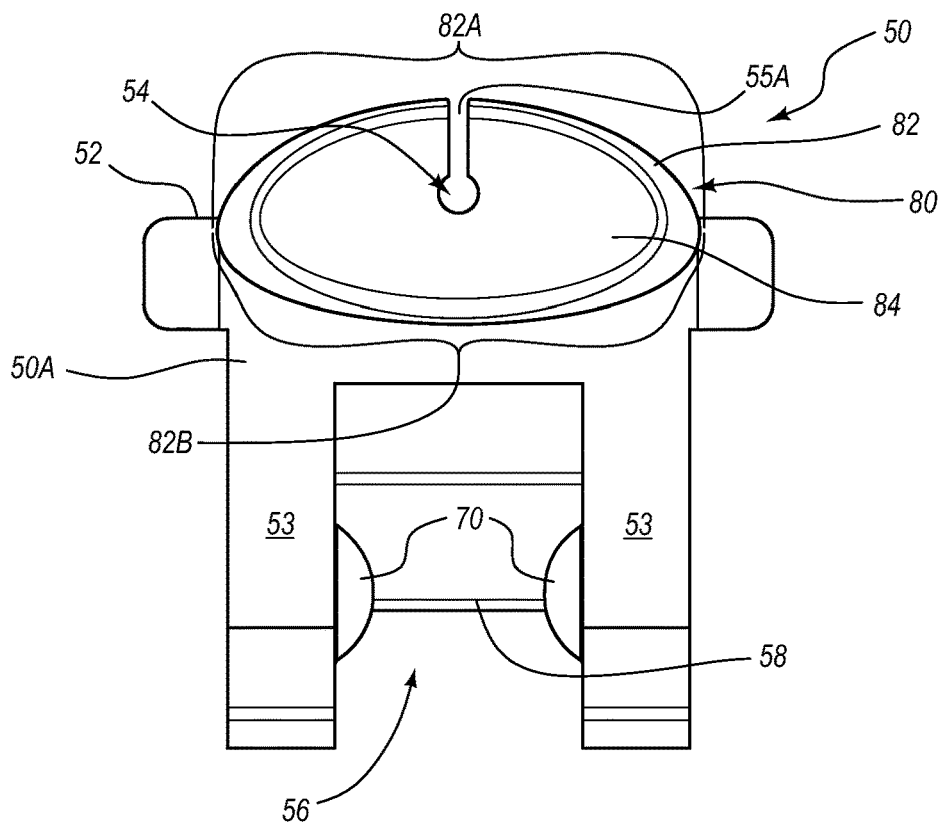
Figure 15D:
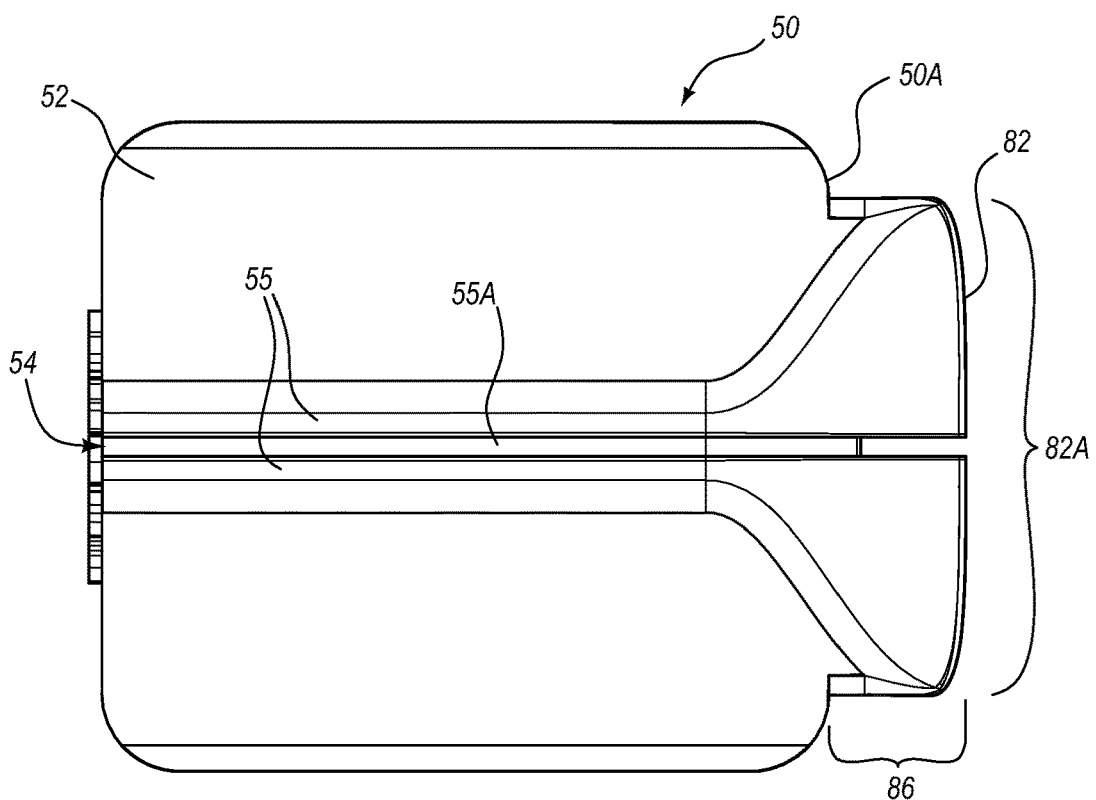
Figure 15E:
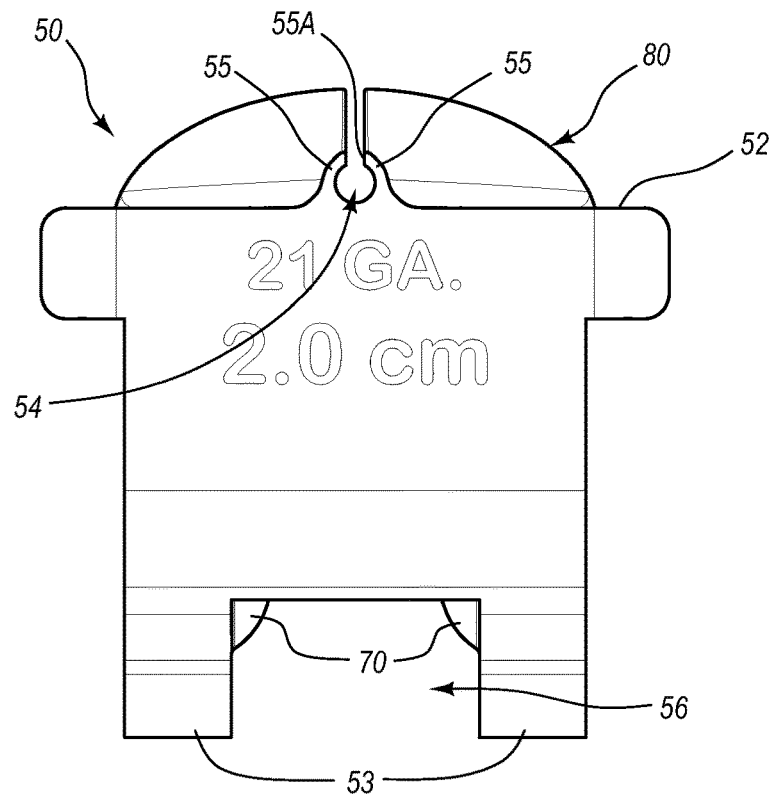
Figure 15F:
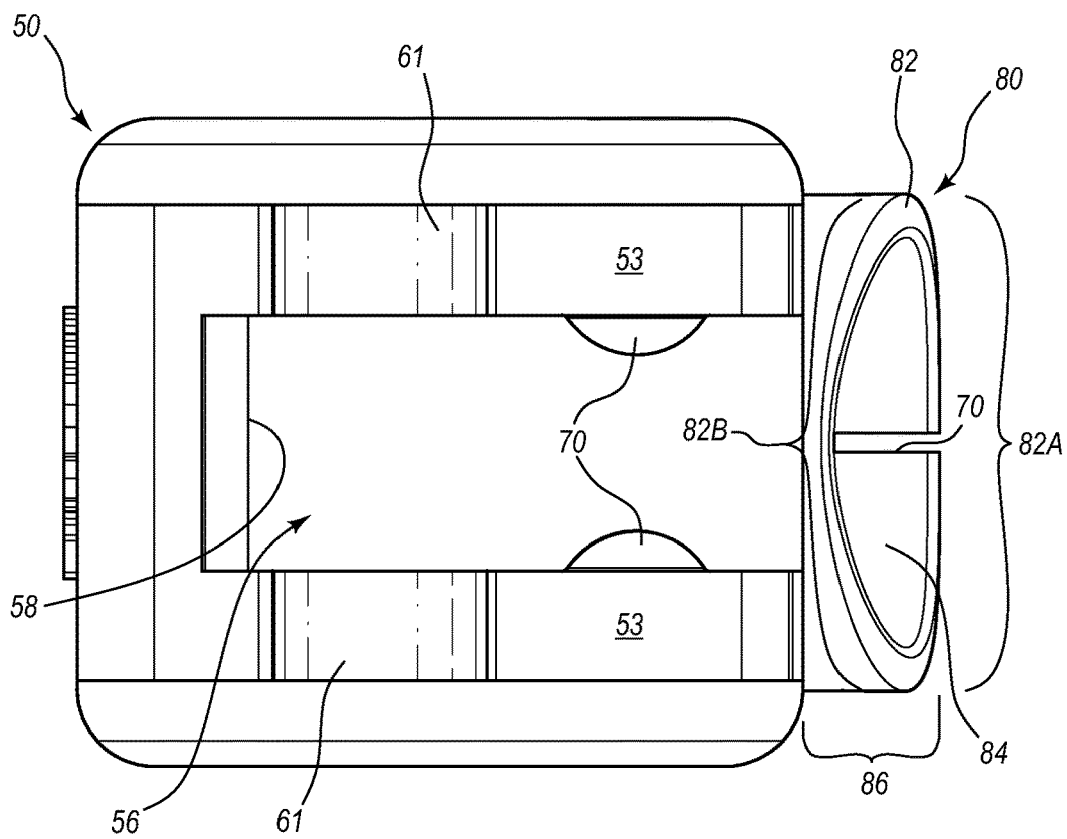

The needle guide 50 defines the cavity 56, best seen in FIGS. 15C and 15F, which is shaped to receive therein a connector, such as the connector 30 of the ultrasound probe 18 in FIGS. 14A-14C, or other apparatus to which the needle guide is to attach. The smoothly shaped extended surface 58 is included at the closed end of the cavity 56 and is configured for interfacing with the overhang portion 34 of the connector 30 of the probe when attached thereto. The extended surface 58 is but one example of a feature included on the needle guide 50 to assist in retaining the needle guide on the connector 30. Note that the needle guide 50 in the present embodiment is removably attachable to a connector disposed on the ultrasound probe, such as in a snap-fit arrangement; in other embodiments, permanent attachment of the needle guide to a probe or other device is possible. In yet another embodiment, the needle guide attaches to a cap or other component that in turn attaches to the probe.

Notches 61 are defined in the legs 53 of the needle guide body, as best seen in FIGS. 15B and 15F and are positioned to respectively receive therein the extensions 36A, 36B of the connector 30 included on the probe 18 (FIGS. 14A-14C). This serves to enhance the stability of the connection between the needle guide 50 and the connector 30 in order to resist undesired needle guide movement while the attached to the probe 18. As mentioned, note that the size, shape, number, and configuration of the notches can vary from what is shown and described herein.

The needle guide 50 further includes two protrusions 70 in the cavity 56 that are sized and positioned to engage with the corresponding two depressions 40 of the needle guide connector 30 on the probe 18 (FIGS. 14A-14C). Note that the size, shape, number, and other configuration details of the needle guide protrusions and cavity itself can vary from what is described herein while still residing within the scope of present embodiments.

The needle channel 54 of FIGS. 15A-15F is shown to be sized for a 21 Gauge needle. In other embodiments, however, the needle channel can be sized to accommodate needles of other sizes and configurations. Also, the needle guide can be configured in one embodiment to accept devices other than needles, such as trocars or catheters for instance.

As mentioned above, the needle guide top surface 52 is oriented such that the needle channel 54 defines an angle with a longitudinal axis of the probe. For instance, the top surface 52 and needle channel 54 of the needle guide 50 shown in FIGS. 15A-15F are angled so as to intercept an extension of the longitudinal axis of the probe 18 at a distance of about two centimeters below the probe head portion 18A. As will be seen, other angles can be defined by the top surface/needle channel. Also, in other embodiments the needle channel can be included on other than the top surface of the needle guide body, such as a side surface, for instance.

The needle guide 50 further includes an extended guide feature for facilitating the ease of insertion of a needle into a proximal end of the needle channel 54. "Extended guide feature" as used herein includes features, components, elements, etc. that enhance the ability for a needle to be guided by a user toward/into the needle channel of the needle guide. In the present embodiment, the extended guide feature includes a guide cone 80, disposed at the proximal end 50A of the needle guide 50, which extends from the top surface 52 of the needle guide 50 and is defined by proximal portions of the lips 55 so as to be in communication with the needle channel 54.

As shown, the guide cone 80 is elliptically funnel-shaped so as to provide a tapered, elliptically conical three-dimensional funnel surface 84 that guides a distal tip of a needle toward the needle channel 54. As such, the guide cone 80 provides a relatively large target easily viewable and accessible by a clinician using the needle guide. This in turn obviates the need for the clinician to remove the probe 18 (FIGS. 14A-14C) from the skin of the patient during ultrasound imaging procedures in order to insert the needle into an otherwise relatively small needle channel of the needle guide attached to the probe. As has been discussed above, such removal of the probe 18 from the skin of the patient is undesired and can undermine the effectiveness of magnetic-based needle insertion guidance systems associated with the ultrasound imaging system, which guidance systems often require the probe not to be moved from the patient's skin after magnetic calibration has been performed.

In greater detail, FIG. 15C shows that the guide cone 80 includes an elliptical perimeter 82 that in turn includes a leading edge 82A and a trailing edge 82B. The leading edge 82A includes approximately half the perimeter 82, i.e., the portion of the perimeter disposed above the top surface 52 of the needle guide 50 from the perspective of FIG. 15C. Thus, the leading edge 82A of the perimeter 82 bounds the portion of the guide cone that is disposed above the needle guide top surface 52, which is also referred to herein as being above in an orthogonal direction with respect to the top surface. The trailing edge 82B of the perimeter 82 bounds the portion of the guide cone 80 that is disposed below the top surface 52 of the needle guide 50, also referred to herein as being below in an orthogonal direction with respect to the top surface.

FIG. 15B shows that a forward extending portion 86 of the guide cone 80 extends beyond the proximal end 50A of the needle guide 50. Further, the leading edge 82A of the perimeter 82 extends proximally further away from the body of the needle guide 50 relative to the trailing edge 82B, with the perimeter being included on the forward extending portion 86. Note, however, that the shape and configuration of the guide cone, its perimeter, and the leading and trailing edges can vary from what is shown and described herein. For instance, the guide cone can define a round funnel shape. In another embodiment, the perimeter of the guide cone can be coincident with the proximal end of the needle guide instead of extending past the proximal end. Note that the needle guide in one embodiment is formed from a suitable thermoplastic, such as low-density polyethylene, though other materials could also be employed. Desired characteristics for the needle guide material in one embodiment include the ability of the material to form a needle channel that is firm enough to retain the needle therein, yet flexible sufficient to enable the lips of the needle channel to deform and release the needle from the needle channel.

Figure 16:
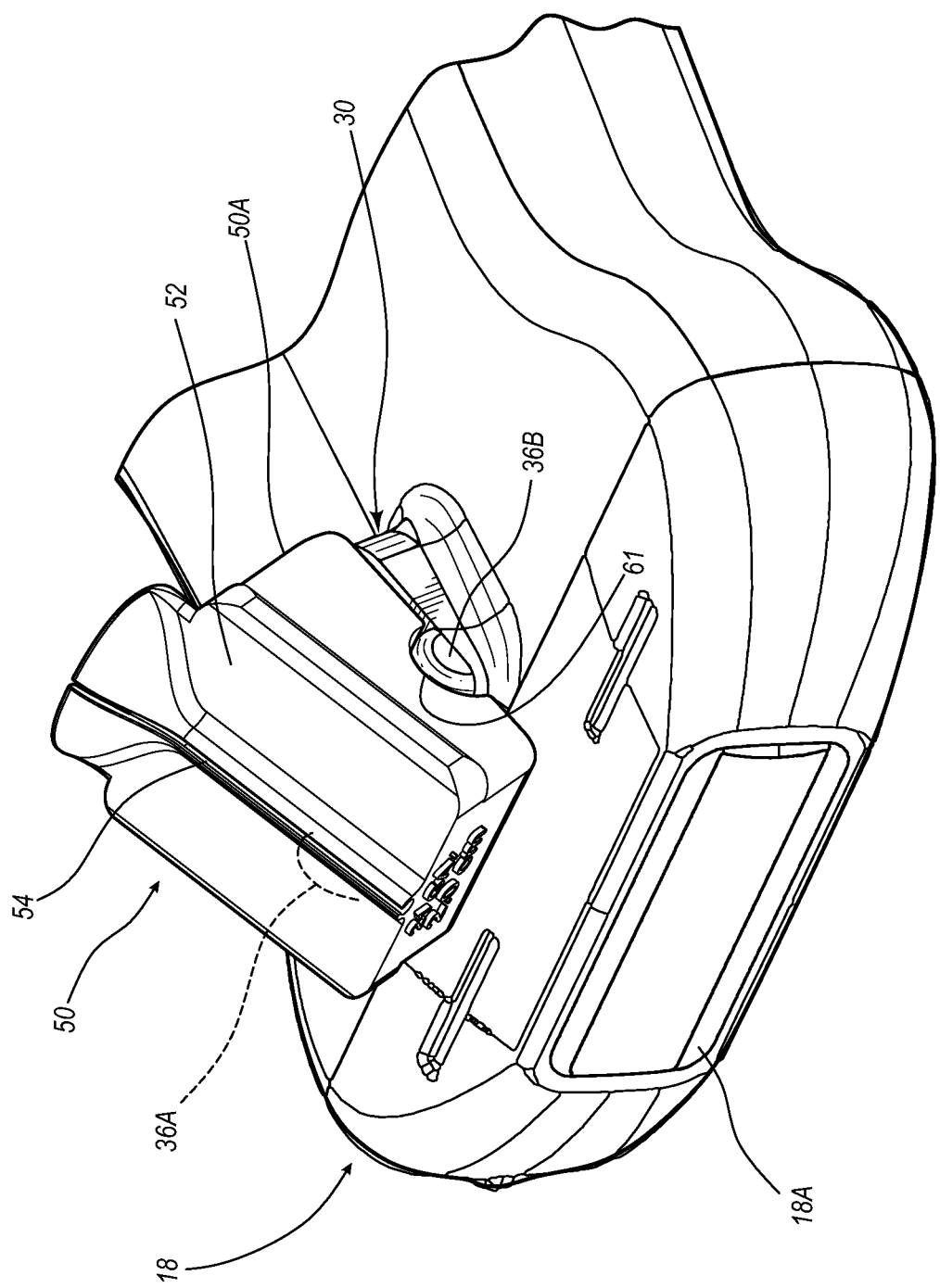
FIG. 16 is a perspective view of an ultrasound probe with the needle guide of FIGS. 15A-15F attached to a connector of the probe.

FIG. 16 depicts the manner of attachment of the needle guide 50 of FIGS. 15A-15F with the connector 30 of FIGS. 14A-14C. As shown, the connector 30 is received within the cavity 56 of the needle guide 50 such that the extended surface 58 in the cavity snap-fits over the overhang 34 of the connector. Additionally, the protrusions 70 disposed in the needle guide cavity 56 are received in the corresponding depressions 40 to further the snap-fit attachment of the needle guide 50 to the connector 30.

In this attached state, FIG. 16 further shows that the notches 61 of the needle guide 50 are positioned to receive therein the corresponding extensions 36A, 36B when the needle guide is attached to the connector 30. So attached, and as with previous embodiments, the stability extensions 36A, 36B of the connector 30 engage the notches 61 to help secure the needle guide in place with respect to the probe 18. Should detachment of the needle guide 50 from the connector 30 be desired, the user can simply pull the needle guide from the connector to overcome the snap-fit arrangement.

Reference is now made to FIGS. 17A-17G. As mentioned above in connection with FIGS. 15A-15F, the needle guide top surface 52 can be oriented such that the needle channel 54 defines an angle with a longitudinal axis of the probe (FIGS. 14A-14C, 16) different from what is shown in FIGS. 15A-15F. In one embodiment, this is achieved by altering the length of the needle guide legs 53, as depicted in FIGS. 17A-17G, which show the needle guide 50 as including legs 53 of varying sizes so as to provide varying needle channel-to-probe longitudinal axis angles. This, in turn, causes a needle disposed through the needle channel 54 to intersect the extension of the probe longitudinal axis at differing distances from the surface of the probe head 18A, according to the needle guide's angle.

Figure 17A:
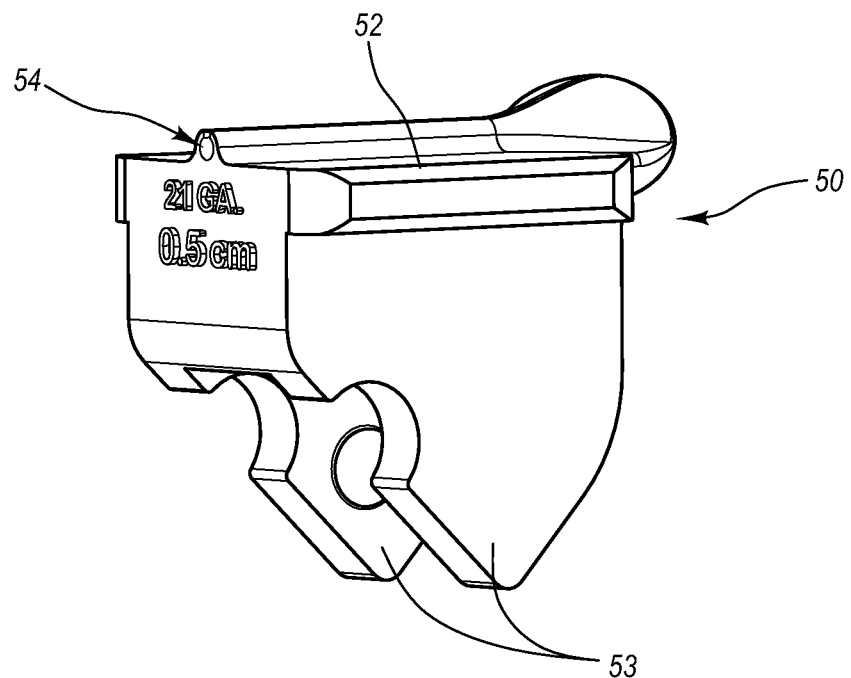
FIGS. 17A-17G are various views of needle guides according to certain embodiments.
Figure 17B:
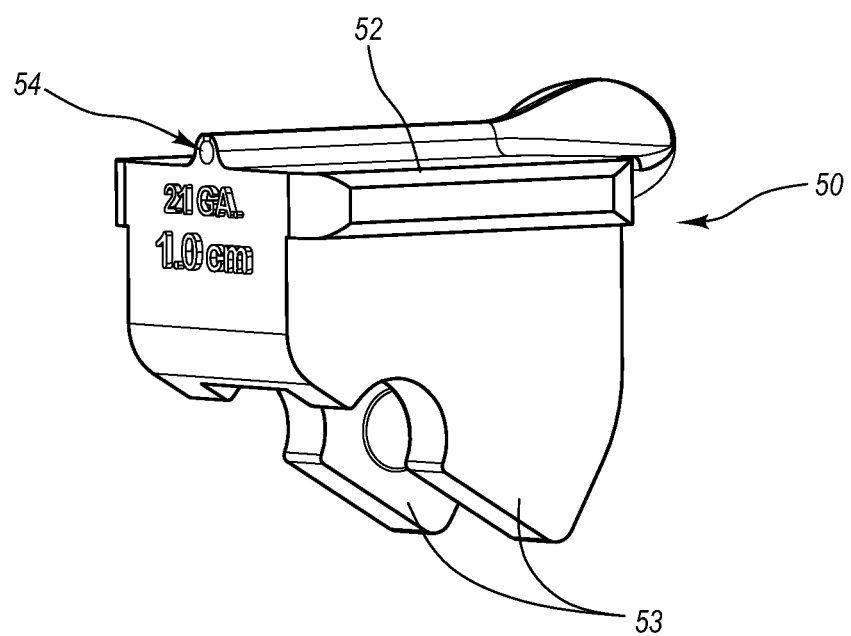
Figure 17C:
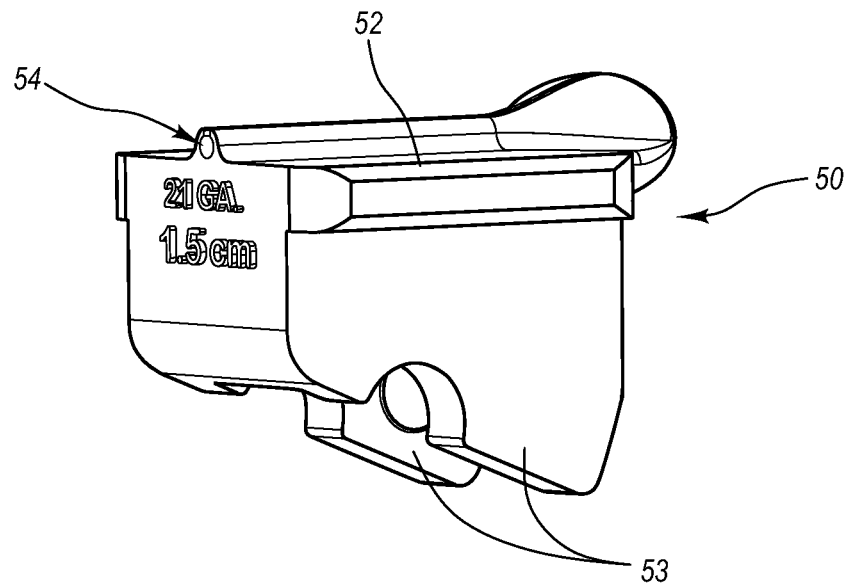
Figure 17D:
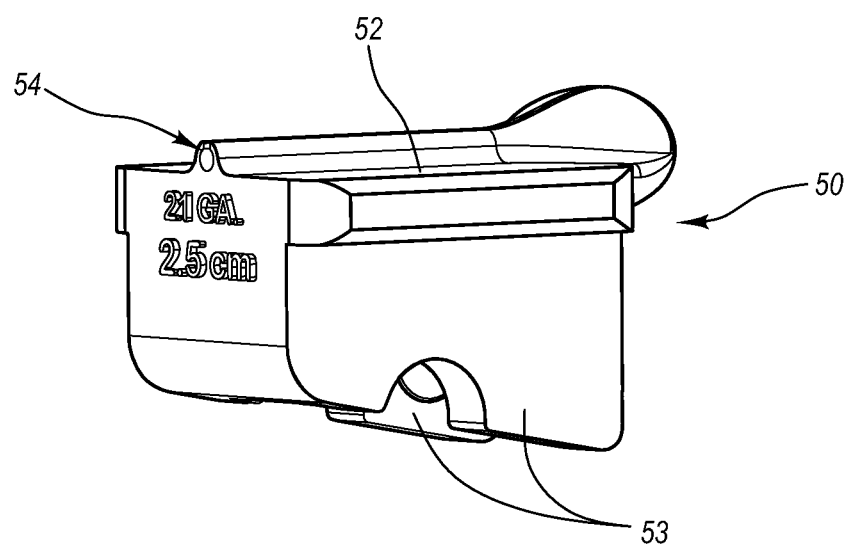
Figure 17E:
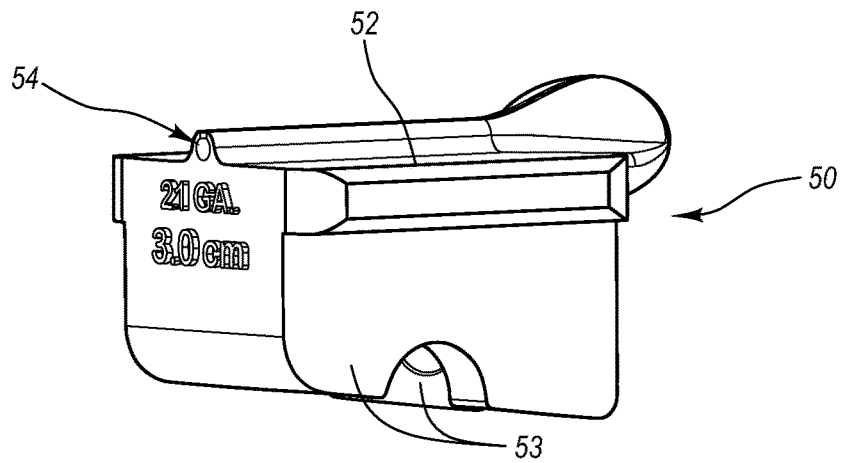
Figure 17F:
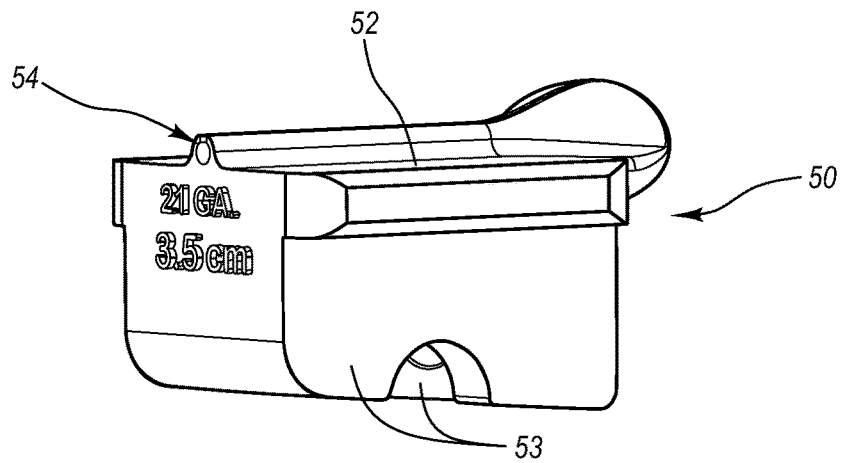
Figure 17G:
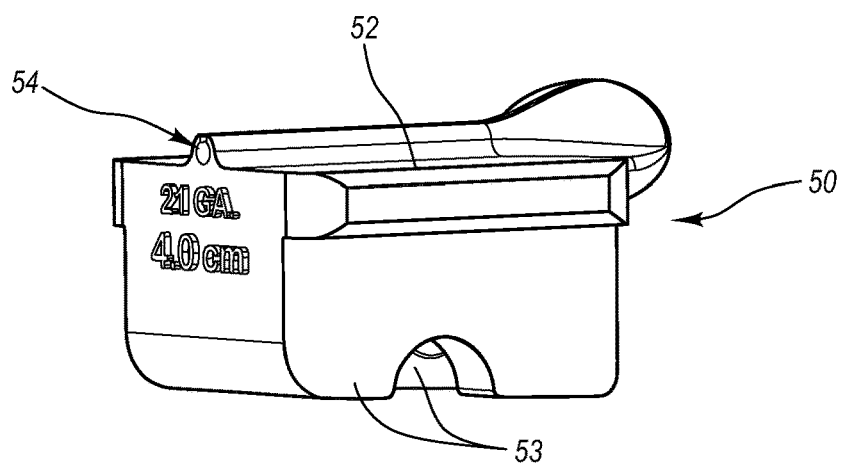

In light of the above, FIGS. 17A-17G show needle guides 50 configured for approximate intersection distances of 0.5 cm (FIG. 17A), 1.0 cm (FIG. 17B), 1.5 cm (FIG. 17C), 2.5 cm (FIG. 17D), 3.0 cm (FIG. 17E), 3.5 cm (FIG. 17F), and 4.0 cm (FIG. 17G).

So configured, multiple needle guides, each having a needle channel defining a unique angle with the longitudinal axis of the probe, can be constructed as to be selectively attachable to/removable from the probe needle guide connector of the probe, enabling a plurality of needle insertion angles to be achieved with the system 10. Of course, other angles are also possible. In another embodiment, more than one needle channel is included on a single needle guide.

Figure 18:
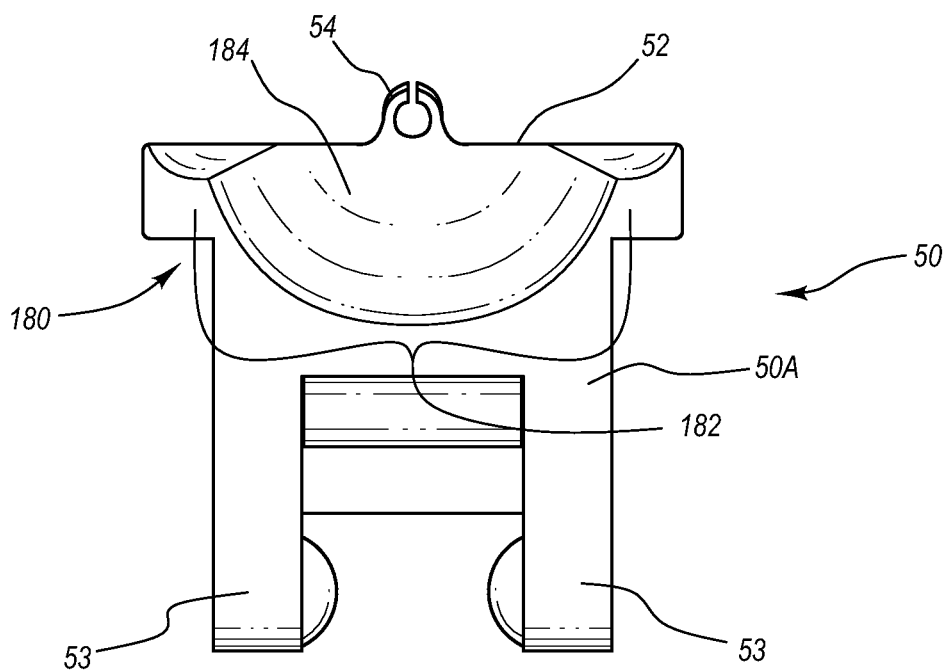
FIG. 18 is an end view of a needle guide according to one embodiment.

FIG. 18 depicts details of the needle guide 50 according to another embodiment, including the legs 53 supporting the top surface 52 on which the needle channel 54 is disposed. The needle guide 50 includes an extended guide feature for assisting in guiding a needle into the needle channel 54. The extended guide feature here includes a concavely shaped guide surface 180 defined on the proximal end 50A of the needle guide 50. The guide surface 180 is defined by a semicircular perimeter 182 such that the guide surface substantially extends the width of the body of the needle guide 50 from the perspective shown in FIG. 18. The perimeter 182 bounds a concavely shaped, conical section surface 184 that funnels toward and is in communication with the needle channel 54.

Figures 19A, 19B:
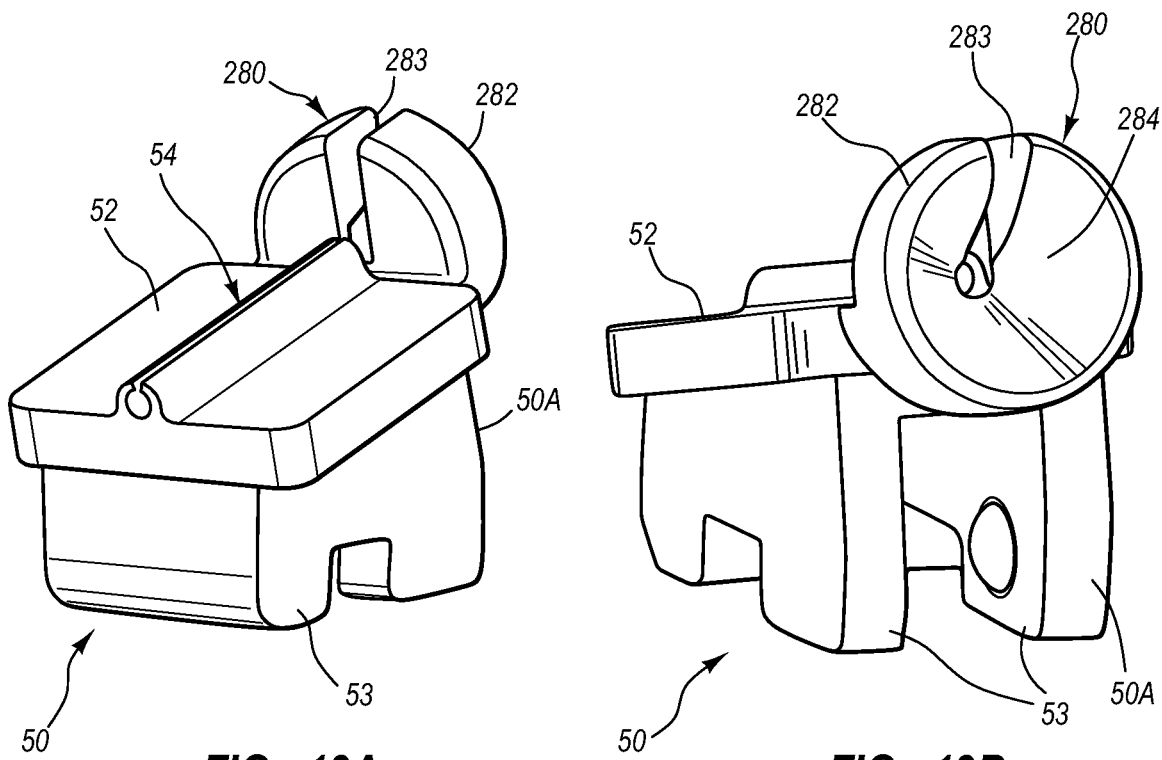
FIGS. 19A and 19B are various views of a needle guide according to one embodiment.

FIGS. 19A and 19B depict details of the needle guide 50 according to another embodiment, including the legs 53 supporting the top surface 52 on which the needle channel 54 is disposed. The needle guide 50 includes an extended guide feature for assisting in guiding a needle into the needle channel 54. The extended guide feature here includes a guide cone 280 having a thickness so as to extend from the proximal end 50A of the needle guide 50. The guide cone 280 is defined by a circular perimeter 282 that bounds a round funnel surface 284 that funnels toward and is in communication with the needle channel 54. A slot 283 is included in the guide cone 280 to enable removal of the needle therefrom.

Figure 20A:
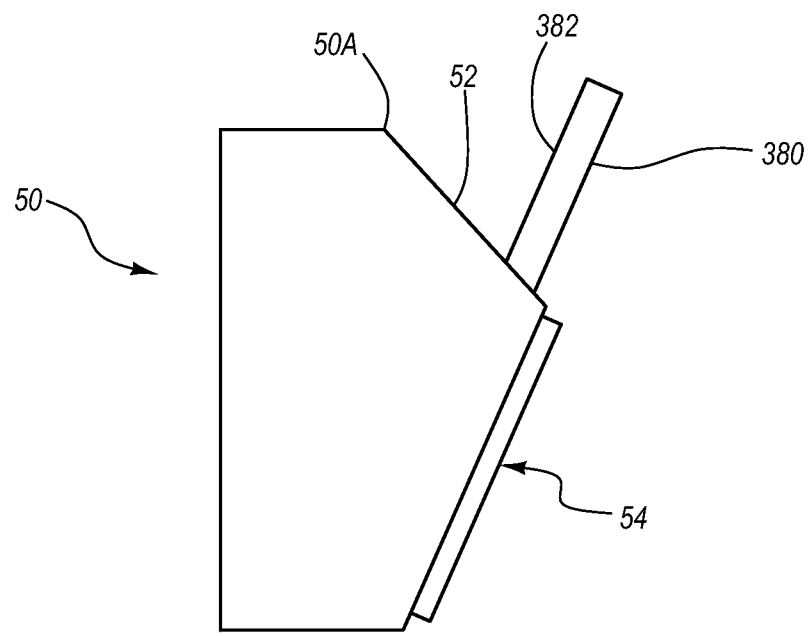
FIGS. 20A and 20B are various views of a needle guide according to one embodiment.
Figure 20B:
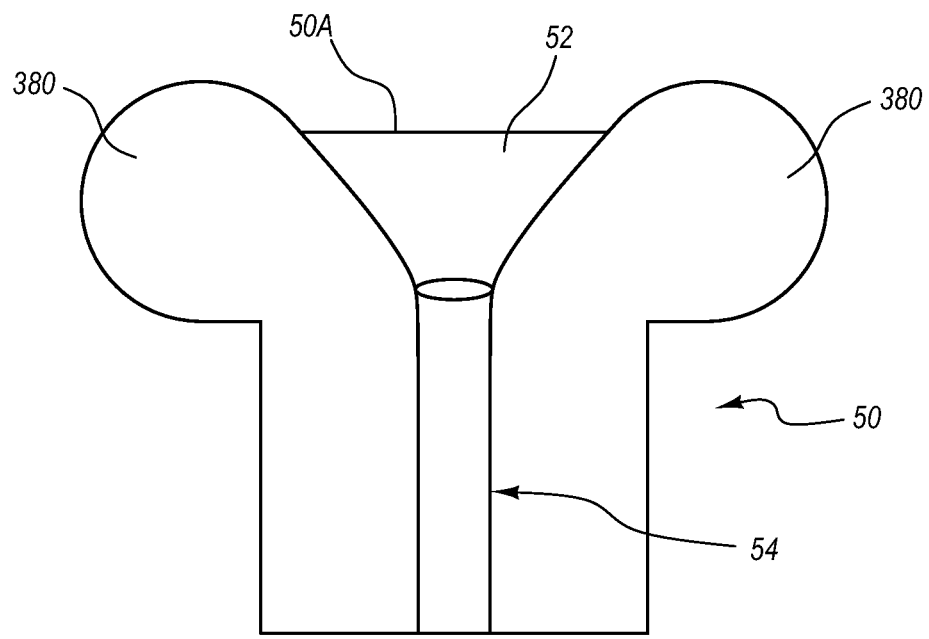

FIGS. 20A and 20B depict details of the needle guide 50 according to another embodiment, including the needle guide body supporting the top surface 52 on which the needle channel 54 is disposed. The needle guide 50 includes an extended guide feature for assisting in guiding a needle into the needle channel 54. The extended guide feature here includes two guide wings 380 that extend proximally from the proximal end 50A of the needle guide 50 in a direction parallel to the top surface 52 such that an upper surface 382 of the guide wings is substantially parallel to the longitudinal orientation of the needle channel 54.

The guide wings 380 are positioned proximate the proximal opening to the needle channel 54 such that a needle that moves atop the upper surface 382 of the guide wings can be inserted into the needle channel with minimal effort. FIG. 20B shows that each of the guide wings 380 is shaped in a wing-like fashion so as to converge toward the proximal opening of the needle channel 54, further guiding the user in directing the needle toward the needle channel. Note that different numbers, sizes, shapes, and configurations of guide wings can be employed with the needle guide.

Figure 21:
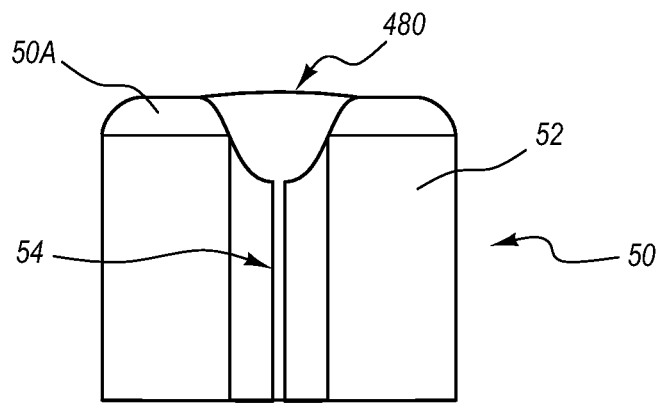
FIG. 21 is a top view of a needle guide according to one embodiment.
Figure 22:
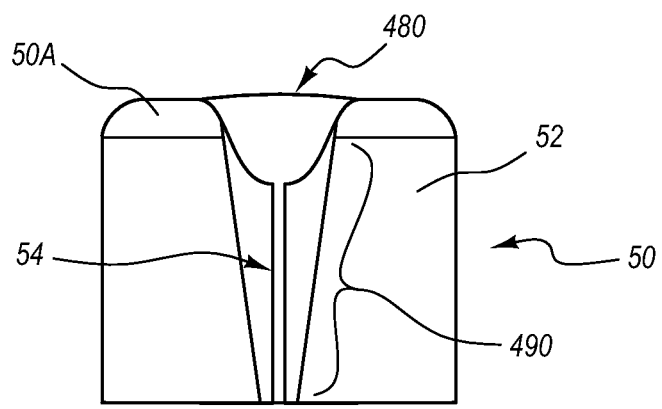
FIG. 22 is a top view of a needle guide according to one embodiment.
Figure 23:
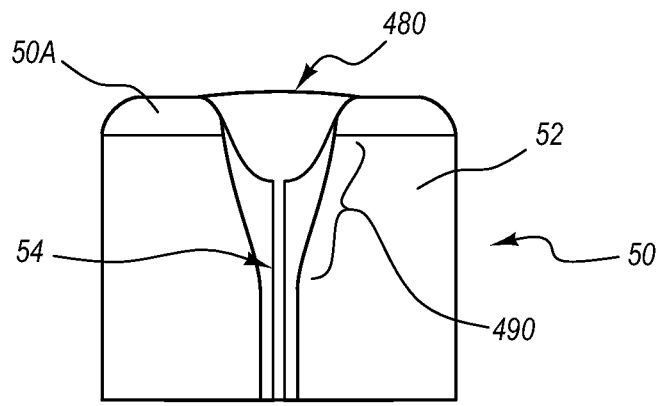
FIG. 23 is a top view of a needle guide according to one embodiment.

FIGS. 21-23 depict additional aspects of the needle guide 50 according to example embodiments. In each of the FIGS. 21-23, the needle guide 50 defines an extended guide feature including a concavely shaped guide surface 480 for guiding a needle into the needle channel 54 disposed on the top surface 52. In FIG. 21 the needle channel 54 is substantially liner. In contrast, the needle channel 54 includes a tapered section 490 wherein a cross sectional area of the needle channel reduces in size from proximal end to distal end thereof. The tapered section 490 in FIG. 22 includes substantially the entirety of the needle channel 54, while in FIG.

23, the tapered section 490 includes approximately only the proximal half of the needle channel, distal to which the needle channel remains substantially linear. It is contemplated that the tapered nature of the needle channel can vary from what is shown and described herein.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A needle guide for use with a handheld probe having a connector protruding from a probe surface, comprising:
   a needle guide body defining:
      a first surface having a proximal end and a distal end; and
      a cavity below the first surface, the cavity shaped to receive the connector;
   a needle channel defined on the first surface from the distal end to a proximal section, the needle channel having a fixed size;
   a guide cone coupled to the needle channel at the proximal section of the first surface, the guide cone having a proximal portion extending beyond the proximal end of the first surface of the needle guide body.

2. The needle guide as defined in claim 1, wherein the guide cone extends below the first surface of the needle guide body in a direction orthogonal to the first surface.

3. The needle guide as defined in claim 1, wherein the guide cone is circularly funnel-shaped.

4. The needle guide as defined in claim 1, wherein the guide cone is elliptically funnel-shaped.

5. The needle guide as defined in claim 4, wherein the elliptical funnel shape of the guide cone is bounded by a perimeter, a leading edge of the perimeter disposed above the first surface of the needle guide in a direction orthogonal to the first surface, and a trailing edge of the perimeter disposed below the first surface of the needle guide in a direction orthogonal to the first surface.

6. The needle guide as defined in claim 1, wherein the needle channel is defined by opposing walls separated by a slot.

7. The needle guide as defined in claim 6, wherein at least a portion of the needle channel is tapered.

8. The needle guide as defined in claim 1, wherein the handheld needle guide body is removably attachable to the handheld probe.

9. The needle guide as defined in claim 8, wherein the handheld probe includes a connector to enable attachment of the needle guide in a snap-fit arrangement.

10. The needle guide as defined in claim 9, wherein the needle guide body defines a cavity for receiving the connector therein.

11. The needle guide as defined in claim 9, wherein the needle guide body defines a plurality of notches that respectively receive a plurality of extensions of the connector so as to stabilize attachment of the needle guide to the connector.

12. The needle guide as defined in claim 1, wherein the handheld probe includes an ultrasound probe and wherein the needle guide removably attaches to the ultrasound probe so as to position the needle channel in an angled configuration with respect to a longitudinal axis of the ultrasound probe.

13. The needle guide as defined in claim 12, wherein the first surface includes a top surface of the needle guide body and wherein the needle guide body includes first and second legs, the first and second legs sized to support the needle channel of the first surface in the angled configuration.

14. The needle guide as defined in claim 4, wherein the elliptical funnel shape of the guide cone is bounded by a perimeter, a leading edge of the perimeter disposed beyond the proximal end of the first surface in a direction parallel to the first surface, a trailing edge of the perimeter disposed distal of the leading edge.

15. The needle guide as defined in claim 1, wherein the needle channel comprises a lumen defined by a needle channel wall.

16. The needle guide as defined in claim 15, wherein the needle channel wall includes a first side, a second side, and a first slot between the first side and the second side.

17. The needle guide as defined in claim 16, wherein the first slot extends an entire length of the needle channel wall from the distal end to the proximal section of the first surface.

18. The needle guide as defined in claim 17, wherein the guide cone includes a second slot in alignment with the first slot.

19. The needle guide as defined in claim 18, wherein the second slot extends an entire length of the guide cone.

20. The needle guide as defined in claim 1, further comprising a continuous slot through the needle channel and the guide cone, the continuous slot extending from a distal end of the needle channel through a proximal end of the guide cone.

21. The needle guide as defined in claim 1, wherein the guide cone includes a slot, and wherein a proximal end of the guide cone includes a continuous perimeter from a first side of the slot to a second side of the slot.

22. The needle guide as defined in claim 1, wherein the needle channel comprises a lumen defined by a needle channel wall and the first surface.

* * * * *